United States Patent
Wilson et al.

(10) Patent No.: US 8,415,144 B2
(45) Date of Patent: Apr. 9, 2013

(54) CELL CULTURE METHODS AND DEVICES UTILIZING GAS PERMEABLE MATERIALS

(75) Inventors: John R. Wilson, New Brighton, MN (US); Douglas A. Page, Eden Prairie, MN (US); Dan Welch, Zimmerman, MN (US); Alison Robeck, Monticello, MN (US)

(73) Assignee: Wilson Wolf Manufacturing, New Brighton, MN (US)

( * ) Notice: Subject to any disclaimer, the term of this patent is extended or adjusted under 35 U.S.C. 154(b) by 801 days.

(21) Appl. No.: 11/505,122

(22) Filed: Aug. 16, 2006

(65) Prior Publication Data

US 2007/0254356 A1 Nov. 1, 2007

Related U.S. Application Data

(62) Division of application No. 10/961,814, filed on Oct. 8, 2004.

(60) Provisional application No. 60/509,651, filed on Oct. 8, 2003.

(51) Int. Cl.
*C12M 1/22* (2006.01)
*C12M 1/00* (2006.01)
*C12M 3/00* (2006.01)

(52) U.S. Cl. ............... 435/305.2; 435/288.3; 435/289.1; 435/303.1; 435/305.1; 435/307.1; 435/304.3; 435/304.2; 435/304.1

(58) Field of Classification Search ............... 435/288.3, 435/289.1, 303.1, 305.1, 307.1, 305.2, 304.3, 435/304.2, 304.1
See application file for complete search history.

(56) References Cited

U.S. PATENT DOCUMENTS

| | | | |
|---|---|---|---|
| 3,459,176 A | 8/1969 | Leonard | |
| 3,839,155 A | 10/1974 | McAleer et al. | |
| 3,853,712 A * | 12/1974 | House et al. | 435/293.2 |
| 3,870,602 A | 3/1975 | Froman et al. | |
| 3,873,423 A | 3/1975 | Munder et al. | |
| 3,941,661 A | 3/1976 | Noteboom | |
| 4,228,243 A | 10/1980 | Iizuka | |
| 4,296,205 A | 10/1981 | Verma | |
| 4,317,886 A | 3/1982 | Johnson et al. | |
| 4,435,508 A | 3/1984 | Gabridge | |
| 4,654,308 A * | 3/1987 | Safi et al. | 435/294.1 |
| 4,661,455 A | 4/1987 | Hubbard | |

(Continued)

FOREIGN PATENT DOCUMENTS

| | | |
|---|---|---|
| CA | 2105419 | 3/1994 |
| DE | 4229334 | 3/1994 |

(Continued)

OTHER PUBLICATIONS

Jensen Mona D., et al., "Diffusion in Tissue Cultures on Gas-permeable and Impermeable Supports", J. Theor,. Biol. 56, 443-458 (1976).

(Continued)

*Primary Examiner* — Nathan Bowers
(74) *Attorney, Agent, or Firm* — Patterson Thuente Pedersen, P.A.

(57) ABSTRACT

Gas permeable devices and methods are disclosed for cell culture, including cell culture devices and methods that contain medium at heights, and certain gas permeable surface area to medium volume ratios. These devices and methods allow improvements in cell culture efficiency and scale up efficiency.

18 Claims, 16 Drawing Sheets

U.S. PATENT DOCUMENTS

| | | | |
|---|---|---|---|
| 4,668,632 A | 5/1987 | Young et al. | |
| 4,717,668 A | 1/1988 | Keilman et al. | |
| 4,734,373 A * | 3/1988 | Bartal | 435/299.2 |
| 4,748,124 A | 5/1988 | Vogler | |
| 4,824,787 A | 4/1989 | Serkes et al. | |
| 4,829,002 A | 5/1989 | Pattillo et al. | |
| 4,829,004 A | 5/1989 | Varani et al. | |
| 4,839,292 A | 6/1989 | Cremonese | |
| 4,847,462 A | 7/1989 | Soodak et al. | |
| 4,906,577 A | 3/1990 | Armstrong et al. | |
| 4,912,058 A | 3/1990 | Mussi et al. | |
| 4,937,194 A | 6/1990 | Pattillo et al. | |
| 4,937,196 A | 6/1990 | Wrasidlo et al. | |
| 4,939,151 A | 7/1990 | Bacehowski et al. | |
| 4,945,203 A | 7/1990 | Soodak et al. | |
| 4,960,706 A | 10/1990 | Bliem et al. | |
| 5,026,650 A | 6/1991 | Schwarz et al. | |
| 5,047,347 A | 9/1991 | Cline | |
| 5,068,195 A | 11/1991 | Howell et al. | |
| 5,078,755 A | 1/1992 | Tozawa et al. | |
| 5,139,951 A | 8/1992 | Butz et al. | |
| 5,153,131 A | 10/1992 | Wolf et al. | |
| 5,173,225 A | 12/1992 | Range et al. | |
| 5,225,346 A | 7/1993 | Matsumiya et al. | |
| 5,240,854 A * | 8/1993 | Berry et al. | 435/305.1 |
| 5,310,676 A | 5/1994 | Johansson et al. | |
| 5,324,428 A | 6/1994 | Flaherty | |
| 5,330,908 A | 7/1994 | Spaulding | |
| 5,426,037 A | 6/1995 | Pannell et al. | |
| 5,437,998 A | 8/1995 | Schwarz et al. | |
| 5,449,617 A | 9/1995 | Falkenberg et al. | |
| 5,503,741 A | 4/1996 | Clark | |
| 5,527,705 A | 6/1996 | Mussi et al. | |
| 5,576,211 A | 11/1996 | Falkenberg et al. | |
| 5,578,492 A | 11/1996 | Fedun | |
| 5,650,325 A | 7/1997 | Spielmann | |
| 5,659,997 A | 8/1997 | Sprehe et al. | |
| 5,670,332 A | 9/1997 | Kuhl et al. | |
| 5,686,301 A | 11/1997 | Falkenberg et al. | |
| 5,686,304 A | 11/1997 | Codner | |
| 5,693,537 A | 12/1997 | Wilson et al. | |
| 5,702,941 A | 12/1997 | Schwarz | |
| 5,702,945 A | 12/1997 | Nagels et al. | |
| 5,707,869 A | 1/1998 | Wolf et al. | |
| 5,714,384 A | 2/1998 | Wilson et al. | |
| 5,783,075 A | 7/1998 | Eddleman et al. | |
| 5,866,400 A | 2/1999 | Palsson et al. | |
| 5,866,419 A | 2/1999 | Meder | |
| 5,876,604 A | 3/1999 | Nemser et al. | |
| 5,902,747 A | 5/1999 | Nemser et al. | |
| 5,914,154 A | 6/1999 | Nemser | |
| 5,924,583 A * | 7/1999 | Stevens et al. | 215/40 |
| 5,928,936 A | 7/1999 | Ingram | |
| 5,935,847 A | 8/1999 | Smith et al. | |
| 5,963,537 A | 10/1999 | Fujisawa | |
| 5,985,653 A | 11/1999 | Armstrong et al. | |
| 5,989,913 A | 11/1999 | Anderson et al. | |
| 6,063,618 A | 5/2000 | Weuster-Botz et al. | |
| 6,130,080 A | 10/2000 | Fuller | |
| 6,150,159 A | 11/2000 | Fry | |
| 6,190,913 B1 | 2/2001 | Singh | |
| 6,228,607 B1 | 5/2001 | Kersten et al. | |
| 6,297,046 B1 | 10/2001 | Smith et al. | |
| 6,306,491 B1 | 10/2001 | Kram et al. | |
| 6,455,310 B1 | 9/2002 | Barbera-Guillem | |
| 6,468,792 B1 | 10/2002 | Bader | |
| 6,562,616 B1 | 5/2003 | Toner et al. | |
| 6,569,675 B2 | 5/2003 | Wall et al. | |
| 6,605,463 B1 | 8/2003 | Bader | |
| 6,759,245 B1 | 7/2004 | Toner et al. | |
| 6,855,542 B2 | 2/2005 | DiMilla et al. | |
| 6,900,055 B1 | 5/2005 | Fuller et al. | |
| 7,229,820 B2 * | 6/2007 | Wilson | 435/284.1 |
| 7,560,274 B1 | 7/2009 | Fuller et al. | |
| 2003/0008388 A1 | 1/2003 | Barbera-Guillem et al. | |
| 2003/0017142 A1 | 1/2003 | Toner et al. | |
| 2003/0077816 A1 | 4/2003 | Kronenthal et al. | |
| 2003/0143727 A1 * | 7/2003 | Chang | 435/289.1 |
| 2003/0157709 A1 | 8/2003 | DiMilla et al. | |
| 2003/0203477 A1 * | 10/2003 | Hyman et al. | 435/289.1 |
| 2004/0029266 A1 | 2/2004 | Barbera-Guillem | |
| 2004/0043481 A1 | 3/2004 | Wilson | |
| 2004/0067585 A1 | 4/2004 | Wang et al. | |
| 2004/0072347 A1 | 4/2004 | Schuler et al. | |
| 2004/0110199 A1 | 6/2004 | Montemagno et al. | |
| 2005/0032205 A1 | 2/2005 | Smith et al. | |
| 2005/0106717 A1 | 5/2005 | Wilson | |
| 2005/0148068 A1 | 7/2005 | Lacey et al. | |
| 2007/0026516 A1 | 2/2007 | Martin et al. | |
| 2008/0176318 A1 | 7/2008 | Wilson | |
| 2008/0206857 A1 | 8/2008 | Kenney et al. | |
| 2008/0227176 A1 | 9/2008 | Wilson | |
| 2009/0160975 A1 | 6/2009 | Kwan | |
| 2010/0055774 A1 | 3/2010 | Wilson | |
| 2010/0255576 A1 | 10/2010 | Wilson | |
| 2011/0287542 A1 | 11/2011 | Wilson | |
| 2011/0287543 A1 | 11/2011 | Wilson | |

FOREIGN PATENT DOCUMENTS

| | | |
|---|---|---|
| EP | 0155237 | 9/1985 |
| EP | 264464 | 4/1988 |
| EP | 353893 | 2/1990 |
| EP | 0647707 | 4/1995 |
| EP | 0700990 | 3/1996 |
| EP | 0 866 122 | 9/1998 |
| EP | 0 890 636 B1 | 10/2001 |
| EP | 1245670 | 10/2002 |
| FR | 2666094 | 2/1992 |
| GB | 2268187 | 1/1994 |
| JP | 59220182 | 12/1984 |
| JP | 62 032875 | 2/1987 |
| JP | 6434283 | 7/1987 |
| JP | 5-123182 | 5/1993 |
| JP | 78267 | 1/1995 |
| JP | 10504710 | 5/1998 |
| JP | 2002-528567 | 9/2002 |
| JP | 2002-335946 | 11/2002 |
| JP | 2003503022 | 1/2003 |
| WO | WO9600780 | 1/1996 |
| WO | WO 9630497 | 10/1996 |
| WO | WO98/17362 | 4/1998 |
| WO | WO9853894 | 12/1998 |
| WO | WO 00/23331 | 4/2000 |
| WO | WO 00/24437 | 5/2000 |
| WO | WO 00/56870 | 9/2000 |
| WO | WO00/58437 | 10/2000 |
| WO | WO0078920 | 12/2000 |
| WO | WO0078932 | 12/2000 |
| WO | WO 01/92462 A1 | 12/2001 |
| WO | WO 02/064730 | 8/2002 |
| WO | WO03/060061 | 7/2003 |
| WO | WO 2008/073314 | 6/2008 |
| WO | WO 2010006055 | 1/2010 |

OTHER PUBLICATIONS

Jensen, Mona D., "Mass cell culture in a controlled environment", Cell Culture and its Applications, Academic Press (1977).

Jensen, Mona D., "Production of Anchorage—Dependent Cells—Problems and their Possible Solutions," Biotechnology and Bioengineering, vol. XXIII, pp. 2703-2716 (1981).

Vogler, E. A., "A Compartmentalized Device for the Culture of Animal Cells", Biomat., Art. Cells, Art. Org., 17(5), 597-610 (1989).

Techno Plastics, Web Catalog (Jan. 2003) http://web.archive.org/web/20031209110901/http://www.tpp.ch/tis.

Machine Translation for Japanese Reference JPH07-034699.

International Search Report for International Application No. PCT/US07/25110 dated May 20, 2008.

International Search Report for International Application No. PCT/US07/25108 dated May 28, 2008.

Written Opinion of the International Searching Authority for International Application No. PCT/US2007/025108 dated May 28, 2008.

Written Opinion of the International Searching Authority for International Application No. PCT/US07/25110 dated May 20, 2008.

International Search Report for International Application No. PCT/US2009/049944 dated Jan. 8, 2010.

Japanese Office Action for Japanese Application No. 2006-534398 date May 25, 2010.
Chinese Office Action for Chinese Application No. 200480032684.8 dated Jul. 1, 2010.
Application and File History for US Publication No. 2005/0106717, published May 19, 2005, inventor Wilson.
Application and File History for US Publication No. 2008/0227176, published Sep. 18, 2008, inventor Wilson.
Application and File History for US Publication No. 2010/0255576 published Oct. 7, 2010, inventor Wilson.
Application and File History for US Publication No. 2008/0176318 published Jul. 24, 2008, inventor Wilson.
Application and File History for US Publication No. 2010/0055774 published Mar. 4, 2010, inventor Wilson.
Giarratana et al., Cell culture bags allow a large extent of ex vivo expansion of LTC-IC and functional mature cells which can subsequently be frozen: interest for large-scale clinical applications. Bone Marrow Transplantation, Oct. 1998, vol. 22, No. 7, pp. 707-715.
CLINIcell®250 commercial product and related User Instructions V-2, date unknown.
LifeCell® X-Fold™ Culture Bag commercial product and related literature, ©2000.
Opticell® commercial product and related literature, ©2000.
OriGen PermaLife™ commercial product and related literature, at least as of Sep. 17, 2004.
VectraCell™ commercial product and related literature, at least as of Sep. 18, 2004.
VueLife™ Culture Bag commercial product and related literature, at least as of Oct. 28, 2003.
petriPERM commercial product and related literature, ©2003.
English Translation of Japanese Office Action (Notice of Reasons for Rejection) for Japanese Application No. 2006-534398 dated Nov. 9, 2010.
Written Opinion from International Application No. PCT/US2009/049944 dated Jan. 20, 2011.
Nagel et al., Membrane-based cell culture systems—an alternative to in vivo production of monoclonal antibodies. Dev Biol Stand, 1999, vol. 101, pp. 57-64.
Secker et al., Gas-permeable lifecell tissue culture flasks give improved growth of Helicobacter pylori in a liquid medium., J Clin Microbial, May 1991, vol. 29, No. 5, pp. 1060-1061.
Canadian Office Action for Canadian Application No. 2,671,812 dated Feb. 28, 2011.
Canadian Office Action for Canadian Application No. 2,671,967 dated Mar. 1, 2011.
Papas et al, "High-Density Culture of Human Islets on Top of Silicone Rubber Membranes" Transplantation Proceedings, vol. 37 (2005) pp. 3412-3414.
EP Publication No. 1687400.
Publication re: VueLife™ Culture bags distributed by CellGeniz, known to applicant at least as early as Sep. 17, 2004. 4 pages.
Genetic Engineering News "OptiCell Concept for Cell Culture Operations". vol. 20, No. 21. Dec. 2000. 4 pages.
US 6,465,252, Oct. 2002, Toner et al. (withdrawn).
European Search Report for European Application No. 11158157.5 dated Dec. 28, 2011.
Machine Translation of JP-05123182 dated May 12, 1993.
Examiner's first report on Australian Patent Application No. 2011200410 dated Aug. 30, 2011.
Budhiono et al., "Kinetic Aspects of Bacterial Cellulose Formation in nata-de-coco Culture System", Carbohydrate Polymers. vol. 40. pp. 137-143 (1999).
Pulvertaft et al, "Activation of Lymphocytes" J. Clin. Path . vol. 20 pp. 795-805 (1967).
Application and File History for U.S. Appl. No. 13/194,298 filed Jul. 29, 2011, inventor Wilson.
Application and File History for U.S. Appl. No. 13/194,363 filed Jul. 29, 2011, inventor Wilson.
Mathiot et al. "Increase of hybridoma productivity using an original dialysis culture system." Cytotechnology, vol. 11 (1993) pp. 41-18.
Babblefish translation of FR 2666094.

\* cited by examiner

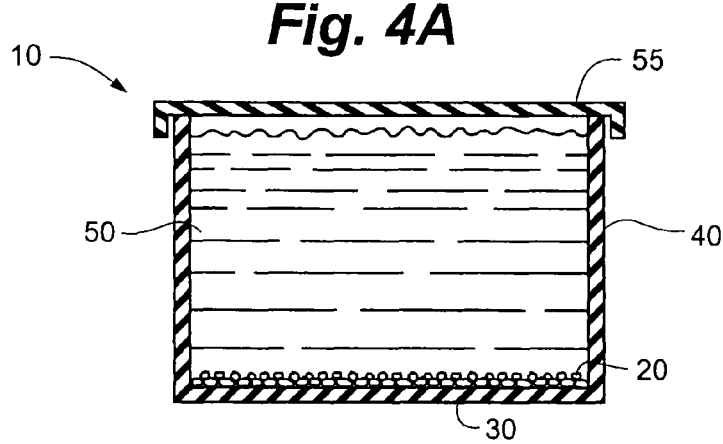
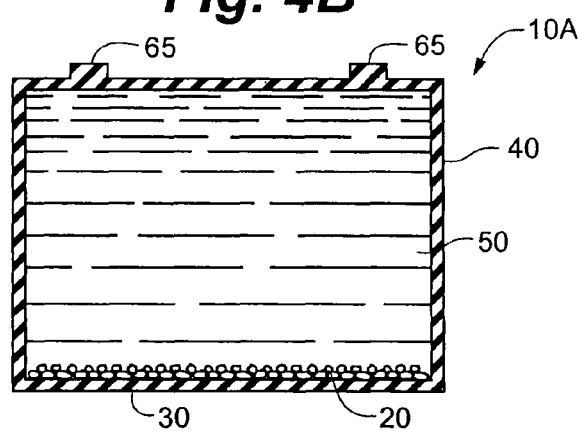
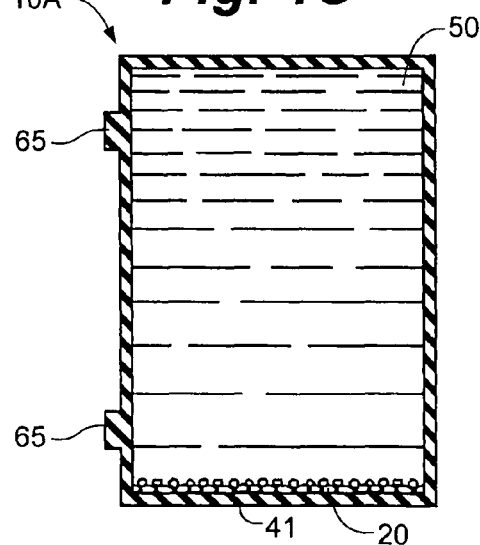

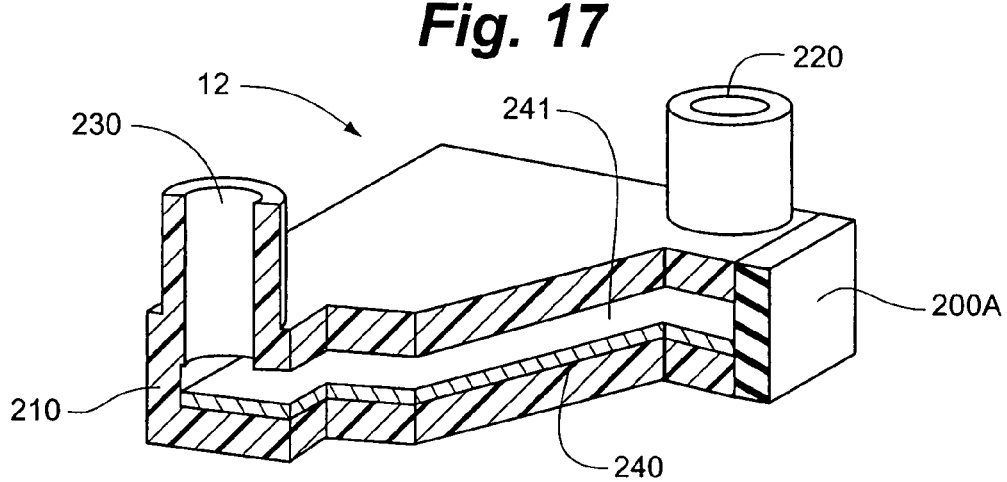
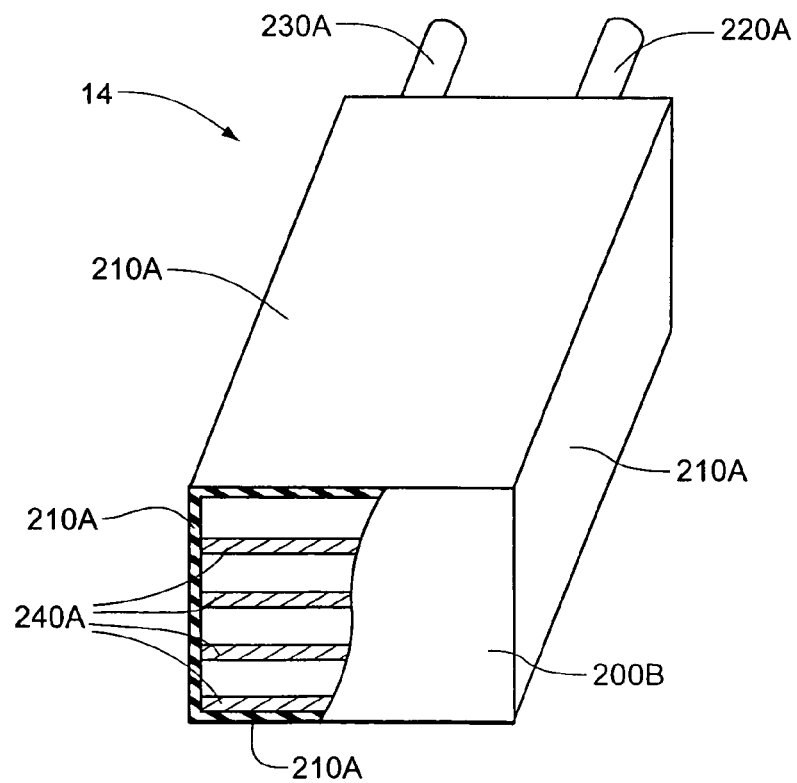

CELL CULTURE METHODS AND DEVICES UTILIZING GAS PERMEABLE MATERIALS

RELATED APPLICATION

This application is a division of application Ser. No. 10/961,814 filed Oct. 8, 2004, which claims the benefit of U.S. Provisional Application No. 60/509,651 filed Oct. 8, 2003.

GOVERNMENT INTERESTS

This invention was made in part with U.S. Government support under National Institutes of Health Small Business Innovative Research Grant 2 R44 GM58978-02A1 "Enhanced Roller Bottle". The U.S. Government may have certain rights in this invention.

TECHNICAL FIELD

The technical field of the invention relates to methods and devices that improve cell culture efficiency. They utilize gas permeable materials for gas exchange, allow an increased height of cell culture medium, reduce the ratio of gas permeable device surface area to medium volume capacity, and integrate traditional cell support scaffolds. A variety of benefits accrue, including more efficient use of inventory space, incubator space, disposal space, and labor, as well as reduced contamination risk.

DISCUSSION OF LIMITATIONS OF CONVENTIONAL TECHNOLOGIES DESCRIBED IN RELATED ART

The culture of cells is a critical element of biotechnology. Cells are cultured in small quantities during the research stage, and typically the magnitude of the culture increases as the research moves towards its objective of benefiting human and animal health care. This increase in magnitude is often referred to as scale up. Certain devices and methods have become well established for research stage cell culture because they allow a wide variety of cell types to be cultured, and are therefore useful to the widest audience. These devices include multiple well tissue culture plates, tissue culture flasks, roller bottles, and cell culture bags. Unfortunately, these devices are inefficient and they become even less efficient in terms of labor, contamination risk, and cost during scale up. There is a need to create alternative devices and methods that research and retain scale up improve research and scale up efficiency. This discussion identifies many of the limitations in conventional technologies and points towards solutions that are subsequently described in more detail.

One attribute that is essential for research scale cell culture is a low level of complexity. Devices that minimize complexity do not require ancillary equipment to mix or perfuse the cell culture medium. They are often referred to as static devices. Static devices can be subdivided into two broad categories, 1) those that are not gas permeable and oxygenate the cells by way of a gas/liquid interface and 2) those that are gas permeable and oxygenate the cells by way of gas transfer through the device housing. The traditional petri dish, multiple well tissue culture plate, tissue culture flask, and multiple shelf tissue culture flask are in the first category. The cell culture bag and compartmentalized flasks are in the second category. All of these static devices are inefficient for a variety of reasons, including the limited height at which medium can reside in them.

Medium height is limited in the petri dish, multiple well tissue culture plate, tissue culture flask, and multiple shelf tissue culture flask due to the method of providing gas exchange. To meet cellular demand, oxygen must diffuse from a gas/liquid interface to the lower surface of the device where cells reside. To ensure adequate oxygen supply, the maximum height of cell culture medium recommended for use in these devices is about 3 mm.

Limited culture medium height leads to disadvantages. It creates a small medium volume, which can only support a small quantity of cells. Medium needs to be continually removed and added to sustain cultures, which increases handling frequency, labor, and contamination risk. The only way to culture more cells in a device is to make the footprint of the device larger so that more medium can be present. Creating a device with large footprint is challenging from a manufacturing standpoint, quickly outgrows the limited amount of space available in a typical incubator and flow hood, and makes the device more difficult to handle. Thus, commercially available cell culture devices are small. Scaling up the culture therefore requires using multiple devices or selecting more sophisticated, complex, and costly alternatives.

The tissue culture flask provides a good example of the problems inherent to static devices that rely upon a gas/liquid interface to function. Tissue culture flasks allow cells to reside upon surfaces typically ranging from 25 $cm^2$ to 225 $cm^2$ in area. The height of medium that is recommended for tissue culture flasks is between 2 mm and 3 mm. For example, Corning® recommends a 45 ml-67.5 ml working volume for its T-225 $cm^2$ flask. Thus, a 1000 ml culture requires between 15 and 22 T-225 $cm^2$ flasks. Not only does this require 15 to 22 devices to be fed, leading to increasing labor and contamination risk, it also makes very inefficient use of space because flasks are designed in a manner that holds about 95% gas and only 5% medium. For example, the body of a typical T-175 flask has a footprint approximately 23 cm long by 11 cm wide, is about 3.7 cm tall, and therefore occupies about 936 $cm^3$ of space. However, it typically operates with no more than about 50 ml of medium. Thus, the medium present in the body (50 ml), relative to the space occupied by the body (936 $cm^3$) demonstrates that nearly 95% of the flask's content is merely gas. This inefficient use of space adds shipping, sterilization, storage, and disposal cost, in addition to wasting precious incubator space.

Another commonly used research scale cell culture device is the multiple well tissue culture plate. As with the traditional tissue culture flask, maintaining a gas/liquid interface at a height of only 2 mm to 3 mm above the bottom of each well is standard operating procedure. In order to provide protection against spillage when the plates are moved around the cell culture laboratory, each well of a typical commercially available 96 well tissue culture plate is about 9 mm deep. The depth increases up to about 18 mm for a six well tissue culture plate. In the case of the ninety-six well plate, gas occupies about 75% of each well and medium occupies about 25% of each well. In the case of the six-well plate, gas occupies about 95% of each well and medium occupies about 5% of each well. This inefficient geometry adds cost to device shipping, sterilization, storage, and disposal.

In many applications, the need to frequently feed the culture by removing and replacing the small volume of medium can be problematic. For example, if the purpose of the multiple well tissue culture plate is to perform experiments, manipulating the medium could affect the outcome of those experiments. Also, because the medium volume is so small, a detrimental shift in solute concentration can occur with just a small amount of evaporation. A multiple well tissue culture plate that allowed medium to reside at an increased height without loss of cell culture function would be superior to the traditional plate by minimizing the manipulations needed to keep the culture alive, and reducing the magnitude of concentration shifts caused by evaporation.

Frequently medium exchange is also time consuming, costly, and leads to elevated contamination risk. Attempts to mitigate the problem by special liquid handling equipment such as multi-channel pipettes do not address the source of the problem, low medium height. The best solution is to allow more medium to reside in each well. Unfortunately, that solution is not possible with traditional plates due to the need for gas exchange by way of the gas/liquid interface.

Better alternatives to traditional devices are needed. If tissue culture devices were available that did not rely solely upon a gas/liquid interface to function, were just as easy to use as traditional flasks and multiple well plates, allowed more cells to be cultured in a device of the same footprint, and were easily and linearly scalable, the efficient gains would translate into reduced costs for those using cells to advance human and animal health care. It will be shown herein how the use of gas permeable materials and novel configurations can achieve this objective.

Cell culture devices that eliminate the gas/liquid interface as the sole source of gas exchange have been proposed, and made their way into the market. This approach relies on the use of a lower gas permeable membrane to bring gas exchange to the bottom of the medium. That, as opposed to sole reliance on gas/liquid interfaces, allows more gas transfer. The proposed and commercially available devices include cell culture bags, compartmentalized gas permeable flasks, gas permeable cartridges, gas permeable petri dishes, gas permeable multiple well plates, and gas permeable roller bottles.

Unfortunately, each of the gas permeable devices has inherent inefficiencies and scale up deficiencies. Primary limitations of cell culture bags, gas permeable cartridges, gas permeable petri dishes, gas permeable multiple well plates, compartmentalized gas permeable flasks, and gas permeable roller bottles include limited medium height, excessive gas permeable surface area to medium volume ratios, and poor geometry for culturing adherent cells. This has the effect of forcing numerous devices to be required for scale up, restricting device design options, and increasing cost and complexity as scale up occurs.

Close examination of prior art surrounding gas permeable devices demonstrates how conventional wisdom, and device design, limits the height of medium and the volume of medium that resides in them. In the 1976 paper entitled Diffusion in Tissue Cultures on Gas-permeable and Impermeable Supports (Jensen et al., J. Theor. Biol. 56, 443-458 (1976)), the theory of operation for a closed container made of gas permeable membrane is analyzed. Jensen et al. describes diffusion as the mode of solute transport in the medium and the paper states that "diffusion proceeds according to Fick's laws." Jensen et al. state "FIG. 2 [of Jensen et al.] shows the diffusional characteristics for cells cultured in a bag made of gas permeable material." FIG. 1A, herein, shows FIG. 2 of Jensen et al. in which $D_cm$ is the diffusion constant of medium. FIG. 1B, herein, shows FIG. 3 of Jensen et al. in which the model of steady state values for $P_{O_2}$ and $P_{CO_2}$ in a gas permeable container are shown as a linear decay throughout the medium, based on diffusion.

In 1977, Jensen (Jensen, Mona D. "Mass cell culture in a controlled environment", Cell Culture and its Applications, Academic Press 1977) described a "major innovation" by the use of "gas permeable, nonporous plastic film" to form a cell culture device. FIG. 2, herein, shows FIG. 2 of Jensen. As shown in FIG. 2, herein, the device created a very low height of medium, only 0.76 mm, and a very high gas permeable surface to medium volume ratio. For scale up, the device gets as long as 30 feet and is perfused using custom equipment.

In 1981, Jensen (Biotechnology and Bioengineering. Vol. XXIII, Pp. 2703-2716 (1981)) specifically stated "culture vessel design must incorporate a small diffusional distance which is fixed and constant for all the cells cultured. The design must be such that scaling-up the culture does not change the diffusion distance." Indeed, the conventional wisdom that medium should not reside at a height very far from the gas permeable membrane continues to this day, as evidenced by the commercial products that utilize gas permeable materials and the patents that are related to them. Furthermore, a high gas permeable surface to medium volume ratio continues.

A variety of gas permeable cell culture devices have entered the market and been proposed since 1981. However, continued reliance on diffusion as a primary design factor appears to be the case based upon review of the patents, device design, device specifications, and operating instructions for gas permeable devices. As design criteria, the model for diffusion limits medium height, leads to high gas permeable surface to medium volume ratios, and contributes to inefficient device geometry.

Commercially available gas permeable cell culture devices in the form of bags are currently a standard device format used for cell culture. As with the configuration of Jensen, these products allow gas exchange through the lower and upper surface of the medium via gas permeable materials. Unlike the device presented by Jensen, perfusion is not required. Typically they are not perfused, and reside in a cell culture incubator. This reduces cost and complexity and has made them an accepted device in the market. However, the limited distance between the gas permeable membranes when cell culture medium resides in them has the effect of making them geometrically unsuitable for efficient scale up. As more medium is needed, bag size must increase proportionally in the horizontal direction. Thus, they are generally unavailable in sizes beyond 2 liters, making numerous devices required for scale up. Furthermore, they are not compatible with the standard liquid handling tools used for traditional devices, adding a level of complexity for those performing research scale culture.

Bags are fabricated by laminating two sheets of gas permeable films together. A typical bag cross-section is shown in FIG. 3 taken from U.S. Pat. No. 5,686,304, which has been commercialized as the Si-Culture™ bag (Medtronic Inc.). A beneficial feature of traditional static cell culture devices is a uniform distribution of medium over the area where cells reside. Those skilled in the art specifically take great care to level incubators for the purpose of ensuring that the medium resides at a constant height throughout the device. By looking at the bag cross-section of FIG. 3, it can be seen how medium does not reside at a uniform height above the entire lower gas permeable film, no matter how level the incubator is. Since the films mate at the perimeter, medium is forced to reside at a different height near the perimeter than elsewhere in the bag. As medium volume increases, the bag begins to take a cylindrical shape and medium distribution becomes worse. Cells can be subjected to potential nutrient gradients due to the non-uniform shape. If too much medium is in the bag, the lower surface will reside in a non-horizontal state. That also creates problems. Suspension cells residing in the bag will not distribute uniformly. Instead, they will gravitationally settle in the low point, pile up, and die as nutrient and oxygen gradients form within the pile. In the case of adherent cells, they will not seed uniformly because the amount of inoculum residing in each portion of the bag will vary. In addition to the geometric problems created if bags are overfilled, the weight of medium in excess of 1000 ml can also damage the bag as described in U.S. Pat. No. 5,686,304. Even if the geometric limitations of bags were overcome, instructions and patents related to the bags and other gas permeable devices indicate a limit exists based on the belief that diffusion barriers prevent devices from functioning when medium resides at too great a height.

Cell culture bags are commercially available from OriGen Biomedical Group (OriGen PermaLife™ Bags), Baxter (Lifecell® X-Fold™ related to U.S. Pat. Nos. 4,829,002, 4,937,194, 5,935,847, 6,297,046 B1), Medtronic (Si-Culture™, U.S. Pat. No. 5,686,304), Biovectra (VectraCell™), and American Fluoroseal (VueLife™ Culture Bag System, covered by U.S. Pat. Nos. 4,847,462 and 4,945,203). The specifications, operating instructions, and/or patents dictate the medium height and the gas permeable surface area to medium volume ratio for each product.

Pattillo et al. (U.S. Pat. Nos. 4,829,002 and 4,937,194 assigned to Baxter International Inc.) states that typically bags are "filled to about one quarter to one half the full capacity, to provide a relatively high ratio of internal surface area of volume of the media and cells, so that abundant oxygen can diffuse into the bag, and carbon dioxide can diffuse out of the bag, to facilitate cell metabolism and growth." In light of Pattillo et al. the best medium height attained for the Baxter Lifecell® X-Fold™ bags is for their 600 $cm^2$ bag, which yields a medium height of 1.0 cm to 2.0 cm and a gas permeable surface area to medium volume ratio of 2.0 $cm^2$/ml to 1.0 $cm^2$/ml.

The product literature for the VectraCell™ bag states "VectraCell 1 L containers can hold up to 500 mL of media. VectraCell 3 L containers can hold up to 1500 mL of media." Thus, as with the Baxter bags, maximum medium capacity is at one half the bags total capacity. Of the various bag sizes offered, the 3 L bag allows the highest medium height, 1.92 cm, and has the lowest gas permeable surface area to medium volume ratio of 1.04 $cm^2$/ml.

A 1.6 cm medium height is recommended for the Si-Culture™ bag in the product literature and specified in U.S. Pat. No. 5,686,304 when it resides on an orbital shaker that physically mixes the medium. That leads to a gas permeable surface area to medium volume ratio of 1.25 $cm^2$/ml when used in a mixed environment. Since mixing is generally used to break up diffusional gradients and enhance solute transfer, one skilled in the art would conclude that medium height should be reduced when this bag is not placed on an orbital shaker.

The product literature for the VueLife™ bag specifically recommends filling VueLife™ Culture Bags with media at a height of no more than one centimeter thick, because "additional media might interfere with nutrient or gas diffusion." Thus, diffusional concerns limit medium height in the VueLife™ bags. That leads to a gas permeable surface area to medium volume ratio of 2.0 $cm^2$/ml at a medium height of 1.0 cm.

The product literature for the OriGen PermaLife™ bags specify nominal volume at a medium height of 1.0 cm, the equivalent height of the VueLife™ bags. Of the various PermaLife™ bags offered, their 120 ml bag offers the lowest gas permeable surface area to medium volume ratio of 1.8 $cm^2$/ml.

The net result of the limited medium height is that culture scale up using these products is impractical. For example, if the Lifecell X-Fold™ bag were scaled up so that is could contain 10L of medium at a medium height of 2.0 cm, its footprint would need to be at least 5000 $cm^2$. Not only is this an unwieldy shape, the footprint can quickly outsize a standard cell culture incubator, leading to the need for custom incubators. Also, the gas transfer area utilized in the bags is larger than necessary because all of these configurations rely upon both the upper and lower surfaces of the bag for gas transfer.

This impractical geometry has restricted the size of commercially available bags. Recommended medium volume for the largest bag from each supplier is 220 ml for the OriGen PermaLife™ bags, 730 ml for the VueLife™ bags, 1000 ml for the Lifecell® X-Fold™ bags, 1500 ml for the VectraCell™ bags, and 2000 ml for the Si-Culture™ bags when shaken. Therefore, scale up requires the use of numerous individual bags, making the process inefficient for a variety of reasons that include increased labor and contamination risk.

Another deficiency with cell culture bags is that they are not as easy to use as traditional flasks. Transport of liquid into and out of them is cumbersome. They are configured with tubing connections adapted to mate with syringes, needles, or pump tubing. This is suitable for closed system operation, but for research scale culture, the use of pipettes is an easier and more common method of liquid handling. The inability to use pipettes is very inconvenient when the desired amount of medium to be added or removed from the bags exceeds the 60 ml volume of a typical large syringe. In that case the syringe must be connected and removed from the tubing for each 60 ml transfer. For example, a bag containing 600 ml would require up to 10 connections and 10 disconnections with a 60 ml syringe, increasing the time to handle the bag and the probability of contamination. To minimize the number of connections, a pump can be used to transfer medium. However, this adds cost and complexity to small-scale cultures. Many hybridoma core laboratories that utilize cell culture bags fill them once upon setup, and do not feed the cells again due to the high risk of contamination caused by these connections and the complexity of pumps.

Matusmiya et al. (U.S. Pat. No. 5,225,346) attempts to correct the problem of liquid transport by integrating the bag with a medium storage room. The culture room and medium storage room are connected and when fresh medium is needed, medium is passed from the medium room to the culture room. While this may help in medium transport, there is no resolution to the limited medium height and high gas permeable surface area to medium volume ratios that limit bag scale up efficiency. The disclosure presents a medium height of 0.37 cm and gas permeable surface area to medium volume ratio of 5.4 $cm^2$/ml.

Cartridge style gas permeable cell culture devices have been introduced to the market that, unlike cell culture bags, have sidewalls. These types of devices use the sidewall to separate upper and lower gas permeable films. That allows uniform medium height throughout the device. Unfortunately, these devices are even less suitable for scale up than bags because they only contain a small volume of medium. The small medium volume is a result of an attempt to create a high gas permeable surface area to medium volume ratio.

One such product called Opticell® is provided by BioChrystal Ltd. This product is a container, bounded on the upper and lower surfaces by a gas permeable silicone film, each with a surface area of 50 $cm^2$. The sidewall is comprised of materials not selected for gas transfer, but for providing the rigidity needed to separate the upper and lower gas membranes. Product literature promotes its key feature, "two growth surfaces with a large surface area to volume ratio." In an article for Genetic Engineering News (Vol. 20 No. 21 Dec. 2000) about this product, patent applicant Barbera-Guillem states "with the footprint of a microtiter plate, the membrane areas have been maximized and the volume minimized, resulting in a space that provides for large growth surfaces with maximum gas interchange." The operating protocol defining how to use this product specifies introduction of only 10 ml of medium, thereby limiting the height at which medium can reside to 0.2 cm. U.S. patent application Ser. No. 10/183,132 (filed Jun. 25, 2002), associated with this device, states a height up to 0.5 inches (1.27 cm) is possible, but more preferred would be a height of about 0.07 to about 0.08 inches (0.18 cm to about 0.2 cm). WO 00/56870, also associated with this device, states a height up to 20 mm is possible, but more preferred would be a height of 4 mm. Even if the greater height of 1.27 cm described in the patent were integrated into the commercial device, that medium height does not exceed that allowed in bags. Furthermore, that would only reduce the gas permeable surface area to medium volume ratio to 1.00 $cm^2$/ml, which is similar to the bag. U.S. patent application Ser. No. 10/183,132 shows a configuration in which only one side of the device is gas permeable. In that configuration, which was not commercialized, a gas permeable surface area to medium volume ratio of 0.79 $cm^2$/ml at a medium height of 0.5 inches (1.27 cm) would be attained, which is somewhat lower than that of cell culture bags. Therefore, despite a sidewall, even when the geometry allows the maximum medium height, there is not improved scale up efficiency relative to bags.

Cartridge style gas permeable cell culture devices have also been introduced to the market by Laboratories MABIO-International®, called CLINIcell® Culture Cassettes. Like the Opticell®, neither the product design nor the operating instructions provide for an increase in medium height, or a reduced gas permeable surface area to medium volume ratio, relative to bags. The operating instructions for the CLINIcell® 25 Culture Cassette state that no more than 10 ml of medium should reside above the lower 25 $cm^2$ gas permeable surface. Since the surface area of the lower gas permeable material is only 25 $cm^2$, that creates a medium height of only 0.4 cm. Also, since the top and bottom of the device are comprised of gas permeable material, there is a high gas permeable surface area to medium volume ratio of 5.0 $cm^2$/ml. The operating instructions for the CLINIcell® 250 Culture Cassette state that no more than 160 ml of medium should reside above the lower 250 $cm^2$ gas permeable surface, leading to a low medium height of 0.64 cm and a high gas permeable surface area to medium volume ratio of 3.125 $cm^2$/ml.

Cartridge style gas permeable cell culture devices have recently been introduced to the market by Celartis, called Petaka™. Like the Opticell® and CLINIcell® Culture Cassettes, these devices also have a sidewall that functions as a means of separating the upper and lower gas permeable films. Unlike those products, it is compatible with a standard pipettes and syringes, so it improves convenience of liquid handling. Yet, neither the product design nor the operating instructions provide for an increase in medium height, or a reduced gas permeable surface area to medium volume ratio, relative to bags. The operating instructions state that no more than 25 ml of medium should reside between the upper and lower gas permeable surfaces, which comprise a total surface area of 160 $cm^2$. Product literature specifies "optimized media/surface area" of 0.156 ml/$cm^2$. Thus, the medium height is only 0.31 cm and the optimized gas permeable surface area to medium volume ratio is 6.4 $cm^2$/ml.

The limitations of the commercially available cartridge style gas permeable devices for scale up become clear when reviewing the maximum culture volume available for these devices. Opticell® provides up to 10 ml of culture volume, CLINIcell® Culture Cassettes provide up to 160 ml of culture volume, and Petaka™ provides up to 25 ml of culture volume. Therefore, just to perform a 1000 ml culture, it would take 100 Opticell® cartridges, 7 CLINIcell® Culture Cassettes, or 40 Petaka™ cartridges.

Vivascience Sartorius Group has introduced gas permeable petri dishes into the market called petriPERM. The petriPERM 35 and petriPERM 50 are products in the form of traditional 35 mm and 50 mm diameter petri dishes respectively. The bottoms are gas permeable. The walls of the petriPERM 35 mm dish and petriPERM 50 mm dish are 6 mm and 12 mm high respectively. Vivascience product specifications show the petriPERM 35 has a gas permeable membrane area of 9.6 $cm^2$ and a maximum liquid volume of 3.5 ml, resulting in a maximum medium height of 0.36 cm., and the petriPERM 50 has a gas permeable membrane area of 19.6 $cm^2$ and a maximum liquid volume of 10 ml, resulting in a maximum medium height of 0.51 cm. The petriPERM products are designed with a cover that allows the upper surface of medium to be in communication with ambient gas, and a lower gas permeable material that allows the lower surface of the medium to be in communication with ambient gas. Thus, the minimum gas permeable surface area to medium volume ratio of the petriPERM 35 is 2.74 $cm^2$/ml and of the petriPERM 50 is 1.96 $cm^2$/ml. Like other gas permeable devices, the petriPERM products are also inefficient for scale up. Just to perform a 1000 ml culture, at least 100 devices are needed. Furthermore, these devices are not capable of being operated as a closed system.

Gabridge (U.S. Pat. No. 4,435,508) describes a gas permeable cell culture device configured with a top cover like a petri dish, designed for high resolution microscopy. The depth of the well is based on the "most convenient size for microscopy", 0.25 inch (0.635 cm). At best, the device is capable of holding medium at a height of 0.635 cm.

Vivascience Sartorius Group has also introduced gas permeable multiple well tissue culture plates called Lumox Multiwell into the market. These products are also distributed by Greiner Bio-One. They are available in 24, 96, and 394 well formats. The bottom of the plate is made of a 50 micron gas permeable film with a very low auto-fluorescence. Wall height of each well is 16.5 mm for the 24-well version, 10.9 mm for the 96-well version, and 11.5 mm for the 384-well version. Maximum working medium height for each well are specified to be 1.03 cm for the 24-well version, 0.97 cm for the 96-well version, and 0.91 cm for the 384-well version. Although medium height is improved relative to traditional multiple well plates, it falls within the limits of other static gas permeable devices.

Fuller et al. (WO 01/92462 A1) presents a gas permeable multiple well plate that increases the surface area of the lower gas permeable silicone material by texturing the surface. However, the wall height is limited to merely that of "a standard microtiter plate", thereby failing to allow an increase in medium height relative to traditional plates.

In general, it would be advantageous if static gas permeable cell culture devices could utilize membranes that are thicker than those used in commercially available devices. Conventional wisdom for single compartment static gas permeable cell culture devices that rely upon silicone dictates that proper function requires the gas permeable material to be less than about 0.005 inches in thickness or less, as described in U.S. Pat. No. 5,686,304. The Si-Culture™ bag is composed of di-methyl silicone, approximately 0.0045 inches thick. Barbera-Guillem et al. (U.S. patent application Ser. No. 10/183, 132) and Barbera-Guillem (WO 00/56870) state that the thickness of a gas permeable membrane can range from less than about 0.00125 inches to about 0.005 inches when the membranes comprised suitable polymers including polystyrene, polyethylene, polycarbonate, polyolefin, ethylene vinyl acetate, polypropylene, polysulfone, polytetrafluoroethylene, or silicone copolymers. Keeping the films this thin is disadvantageous because the films are prone to puncture, easily get pinholes during fabrication, and are difficult to fabricate by any method other than calendaring which does not allow a profile other than sheet profile. It will be shown herein how an increased thickness of silicone beyond conventional wisdom does not impede cell culture.

Improved static gas permeable devices are needed. If gas permeable devices were capable of scale up in the vertical direction, efficiency would improve because a larger culture could be performed in a device of any given footprint, and more ergonomic design options would be available.

Compartmentalized, static gas permeable devices, are another type of product that provides an alternative to traditional culture devices. However, they also are limited in scale up efficiency by medium height limitations and excessive gas permeable surface area to medium volume ratios. These types of devices are particularly useful for creating high-density culture environments by trapping cells between a gas permeable membrane and a semi-permeable membrane. Although not commercialized, Vogler (U.S. Pat. No. 4,748,124) discloses a compartmentalized device configuration that places cells in proximity of a gas permeable material and contains non-gas permeable sidewalls. The cell compartment is comprised of a lower gas permeable material and is bounded by an upper semi-permeable membrane. A medium compartment resides directly and entirely above the semi-permeable membrane. A gas permeable membrane resides on top of the medium compartment. Medium is constrained to reside entirely above the gas permeable bottom of the device. The patent describes tests with a cell culture compartment comprised of 0.4 cm sidewalls, a medium compartment comprised of 0.8 cm sidewalls, a cell culture volume of 9 ml, a basal medium volume of 18 ml, a lower gas permeable membrane of 22 cm$^2$, and an upper gas permeable membrane of 22 cm$^2$. That creates a cell compartment medium height of 0.4 cm and allows medium to reside at a height of 0.8 cm in the medium compartment. Furthermore, there is a high total gas permeable surface area to total medium volume ratio of 1.63 cm$^2$/ml. In a paper entitled "A Compartmentalized Device for the Culture of Animal Cells" (Biomat., Art. Cells, Art. Org., 17(5), 597-610 (1989)), Vogler presents biological results using the device of U.S. Pat. No. 4,748,124. The paper specifically cites the 1976 Jensen et al. and 1981 Jensen papers as the "theoretical basis of operation." Dimensions for test fixtures describe a 28.7 cm$^2$ lower and 28.7 cm$^2$ upper gas permeable membrane, a cell compartment wall height of 0.18 cm allowing 5.1 ml of medium to reside in the cell compartment, and a medium compartment wall height of 0.97 cm allowing 27.8 ml of medium to reside in the medium compartment. Total medium height is limited to 0.18 cm in the cell compartment, 0.97 cm in the medium compartment, with a high total gas permeable surface area to total medium volume ratio of 1.74 cm$^2$/ml.

Integra Biosciences markets compartmentalized gas permeable products called CELLine™. As with Vogler's device, the cell compartment is bounded by a lower gas permeable membrane and an upper semi-permeable membrane. However, unlike the Vogler geometry, all medium in the device does not need to reside entirely above the gas permeable membrane. Only a portion of the basal medium need reside above the semi-permeable membrane. The patents that cover the Integra Biosciences products, and product literature, describe the need to keep the liquid height in the cell compartment below about 15 mm. A ratio of 5 ml to 10 ml of nutrient medium per square centimeter of gas permeable membrane surface area is described for proper cell support (U.S. Pat. No. 5,693,537 and U.S. Pat. No. 5,707,869). Although the increase in medium volume to cell culture area is advantageous in terms of minimizing the frequency of feeding, in practice the medium height above each centimeter of gas permeable surface area is limited. The commercial design of the devices covered by these patents demonstrates that they, like the other gas permeable devices, limit the amount of medium that can reside above the cells. Over half of the medium volume resides in areas not directly above the semi-permeable membrane in order to reduce the height of medium residing directly above the cells. The non-gas permeable sidewalls of the device are designed so that when the device is operated in accordance with the instructions for use, the height at which medium resides above the semi-permeable membrane in the CELLine™ products is approximately 5.2 cm in the CL1000, 3.5 cm in the CL350, and 1.1 cm in the CL6Well. When operated in accordance with the instructions for use, the height of medium residing in the cell culture compartment is 15 mm for the CL1000, 14 mm for the CL350, and 26 mm for the CL6Well. The patents describe, and the devices integrate, a gas/liquid interface at the upper surface of the medium. Thus, the gas transfer surface area to medium volume ratio is also limited because gas transfer occurs through the bottom of the device and at the top of the medium. The gas transfer surface area to medium volume ratio for each device is approximately 0.31 cm$^2$/ml for the CL1000, 0.32 cm$^2$/ml for the CL350, and 1.20 cm$^2$/ml for the CL6Well.

Bader (U.S. Pat. No. 6,468,792) also introduces a compartmentalized gas permeable device. Absent sidewalls, it is in the form of a bag. It is compartmentalized to separate the cells from nutrients by a microporous membrane. As with the other compartmentalized gas permeable devices, medium height is limited. U.S. Pat. No. 6,468,792 states although medium heights up to 1 to 2 cm can be achieved in the apparatus, actual heights need to be tailored based upon the O2 supply as a function of "medium layer in accordance with Fick's law of diffusion." Since the upper and lower surfaces of the bag are gas permeable, a minimum total gas permeable surface area to total medium volume ratio of 1.0 cm$^2$/ml is attained when the apparatus is filled to its maximum capacity.

If compartmentalized gas permeable devices were capable of increasing their scale up potential in the vertical direction, they would have a more efficient footprint as the magnitude of the culture increases. A static, compartmentalized, gas permeable device that accommodates vertical scale up is needed.

Gas permeable devices that attempt to improve efficiency relative to static gas permeable devices have been introduced. The devices operate in a similar manner as the traditional roller bottle and attempt to improve mass transfer by medium mixing that comes with the rolling action. However, efficient scale up is not achieved. One reason is that, like static devices, design specifications constrain the distance that medium can reside from the gas permeable device walls. This limits device medium capacity. Thus, multiple devices are needed for scale up.

Spaulding (U.S. Pat. No. 5,330,908) discloses a roller bottle configured with gas permeable wall that is donut shaped. The inner cylinder wall and the outer cylinder wall are in communication with ambient gas. The gas permeable nature of the walls provides oxygen to cells, which reside in the compartment bounded by the inner and outer cylinder walls. The cell compartment is filled completely with medium, which is advantageous in terms of limiting cell shear. Spaulding states "the oxygen efficiency decreases as a fiction of the travel distance in the culture media and effectiveness is limited to about one inch or less from the oxygen surface." Thus, the design limits stated by Spaulding include keeping the distance between the inner cylindrical wall and the outer cylindrical wall at 5.01 cm or less in order to provide adequate oxygenation. In that manner, cells cannot reside more than 2.505 cm from a gas permeable wall. That also leads to a gas permeable surface area to medium volume ratio of about 0.79 $cm^2$/ml. Furthermore, the need to have a hollow gas permeable core wastes space. The device only has an internal volume of 100 ml of medium for every 5 cm in length, as opposed to 500 ml for a traditional bottle of equivalent length. The medium volume limitation makes this device less efficiently scalable than the traditional roller bottle, because more bottles are needed for a culture of equivalent volume. Another problem with the device is the use of etched holes, 90 microns in diameter, for gas transfer. These holes are large enough to allow gas entry, but small enough to prevent liquid from exiting the cell compartment. However, they could allow bacterial penetration of the cell compartment since most sterile filters prevent particles of 0.45 microns, and more commonly 0.2 microns, from passing.

In a patent filed in December 1992, Wolf et al. (U.S. Pat. No. 5,153,131) describes a gas permeable bioreactor configured in a disk shape that is rolled about its axis. The geometry of this device attempts to correct a deficiency with the proposal of Schwarz et al. U.S. Pat. No. 5,026,650. In U.S. Pat. No. 5,026,650, a gas permeable tubular insert resides within a cylindrical roller bottle and the outer housing is not gas permeable. Although it was successful at culturing adherent cells attached to beads, Wolf et al. state that it was not successful at culturing suspension cells. The device is configured with one or both of the flat ends permeable to gas. The disk is limited to a diameter of about 6 inches in order to reduce the effects of centrifugal force. The inventors state "the partial pressure or the partial pressure gradient of the oxygen in the culture media decreases as a function of distance from the permeable membrane", which is the same thought process expressed by Jensen in 1976. They also state "a cell will not grow if it is too far distant from the permeable membrane." Therefore, the width is limited to less than two inches when both ends of the disk are gas permeable. These dimensional limitations mean that the most medium the device can hold is less than 1502 ml. Therefore, more and more devices must be used as the culture is scaled up in size. Also, the gas permeable surface area to medium volume ratio must be at least 0.79 ml/$cm^2$ and cells must reside less than 1.27 cm from a gas permeable wall. Furthermore, the device does not adapt for use with existing laboratory equipment and requires special rotational equipment and air pumps.

In a patent filed in February 1996, Schwarz (U.S. Pat. No. 5,702,941) describes a disk shaped gas permeable bioreactor with gas permeable ends that rolls in a similar manner as a roller bottle. Unfortunately, as with U.S. Pat. No. 5,153,131, the length of the bioreactor is limited to about 2.54 cm or less. Unless all surfaces of the bioreactor are gas permeable, the distance becomes even smaller. Maximum device diameter is 15.24 cm. Thus, the gas permeable surface area to medium volume ratio must be at least 0.79 ml/$cm^2$ and cells can never reside more than 1.27 cm from a gas permeable wall. Even with the rolling action, this does not render a substantial reduction in the gas permeable surface area to medium ratio relative to traditional static culture bags, and requires more and more devices to be used as the culture is scaled up in size.

A commercially available product line from Synthecon Incorporated, called the Rotary Cell Culture System™, integrates various aspects of the Spaulding, Schwarz, and Wolf et al. patents. The resulting products are have small medium capacity, from 10 ml to 500 ml, require custom rolling equipment, are not compatible with standard laboratory pipettes, and are very expensive when compared to the cost of traditional devices that hold an equal volume of medium. Thus, they have made little impact in the market because they do not address the need for improved efficiency in a simple device format.

Falkenberg et al. (U.S. Pat. Nos. 5,449,617 and 5,576,211) describes a gas permeable roller bottle compartmentalized by a dialysis membrane. The medium volume that can be accommodated by the bottle is 360 ml, of which 60 ml resides in the cell compartment and 300 ml in the nutrient compartment. In one embodiment, the ends of the bottle are gas permeable. U.S. Pat. No. 5,576,211 states the when the end of the bottle is gas permeable, "gas exchange membranes with a surface area of a least 50 $cm^2$ have been proven to be suitable for cell cultures of 35 ml." Therefore, the minimum gas permeable surface area to volume ratio is 1.43 $cm^2$/ml. In another embodiment, the body of the bottle is gas permeable, with a surface area of 240 $cm^2$. That gas permeable surface oxygenates the entire 360 ml volume of medium that resides in the vessel. Therefore, the minimum gas permeable surface area to volume ratio is 0.67 $cm^2$/ml. The diameter of the bottle is approximately 5 cm, and the length of the bottle is approximately 15 cm. Thus, the bottle is much smaller than a traditional roller bottle, which has a diameter of approximately 11.5 cm and a length up to approximately 33 cm. Although this device is useful for high-density suspension cell culture, its limited medium capacity fails to reduce the number of devices needed for scale up. Furthermore, it is not suitable for adherent culture because it makes no provision for attachment surface area.

Falkenberg et al. (U.S. Pat. No. 5,686,301) describes an improved version of the devices defined in U.S. Pat. Nos. 5,449,617 and 5,576,211. A feature in the form of collapsible sheathing that prevents damage by internal pressurization is disclosed. Gas is provided by way of the end of the bottle and can "diffuse into the supply chamber" by way of the gas permeable sheathing. Unfortunately, it fails to reduce the number of devices needed for scale up because the bottle dimensions remain unchanged. Furthermore, it remains unsuitable for adherent culture.

Vivascience Sartorius Group sells a product called the miniPERM that is related to the Falkenberg et al. patents. The maximum cell compartment module is 50 ml and the maximum nutrient module is 400 ml. Thus, the maximum volume of medium that can reside in the commercial device is 450 ml. The small size of the commercial device, combined with the need for custom rolling equipment, renders it an inefficient solution to the scale up problem.

There exists a need to improve the rolled gas permeable devices so that they can provide more medium per device, thereby reducing the number of devices needed for scale up. That can be achieved if a decreased gas permeable surface area to medium volume ratio is present. Another problem is that non-standard laboratory equipment is needed for operation of the existing devices. The use of standard laboratory equipment would also allow more users to access the technology.

The prior discussion has focused on design deficiencies that limit efficient scale up in existing and proposed cell culture devices. In addition to the previously described limitations, there are additional problems that limit scale up efficiency when adherent cell culture is the objective.

For traditional static devices that rely upon a gas/liquid interface for oxygenation, the adherent cell culture inefficiency is caused by limited attachment surface area per device. For example, only the bottom of the device is suitable for cell attachment with petri dishes, multiple well plates, and tissue culture flasks. The traditional flask provides a good example of the problem. As described previously, a typical T-175 flask occupies about 936 cm$^3$. Yet, it only provides 175 cm$^2$ of surface area for adherent cells to attach to. Thus, the ratio of space occupied to growth surface, 5.35 cm3/cm$^2$, is highly inefficient.

Products that attempt to address the surface area deficiency of traditional flasks are available. Multi-shelved tissue culture flasks, such as the NUNC™ Cell Factory (U.S. Pat. No. 5,310,676) and Corning CellStack™ (U.S. Pat. No. 6,569, 675), increase surface area is by stacking polystyrene shelves in the vertical direction. The devices are designed to allow medium and gas to reside between the shelves. This reduces the device footprint relative to traditional flasks when increasing the number of cells being cultured. The profile of the multi-shelved flasks is also more space efficient that traditional flasks. For example, the space between shelves of the NUNC™ Cell Factory is about 1.4 cm, as opposed to the 3.7 cm distance between the bottom and top of a typical T-175 flask. The reduced use of space saves money in terms of sterilization, shipping, storage, incubator space, and device disposal. This style of device also reduces the amount of handling during scale up because one multi-shelved device can be fed as opposed to feeding multiple tissue culture flasks. Furthermore, the use of traditional polystyrene is easily accommodated. Unfortunately, the device is still sub-optimal in efficiency since each of its shelves requires a gas/liquid interface to provide oxygen.

CellCube® is an adherent cell culture device available from Corning Life Sciences. It is configured in a similar manner to the multiple shelved tissue culture flasks, but it eliminates the gas/liquid interface. The distance between the vertically stacked cell attachment shelves is therefore reduced because gas is not present. That reduces the amount of space occupied by the device. However, in order to provide gas exchange, continuous perfusion of oxygenated medium is required. That leads to a very high level of cost and complexity relative to the Coming CellStack™, rendering it inferior for research scale culture.

Static gas permeable devices do not provide a superior alternative to the NUNC™ Cell Factory, Coming CellStack™, or CellCube®. Cell culture bags and gas permeable cartridges can provide more attachment area than traditional tissue culture flasks. That is because they could allow cells to be cultured on both the upper and lower device surfaces. However, gas permeable materials that are suitable for cell attachment can be much more expensive than traditional polystyrene. Also, even if both the upper and lower surfaces of a gas permeable device allowed cells to grow, only a two-fold increase in surface area would be obtained relative to a traditional gas/liquid interface style device that occupied the same footprint. Furthermore, the scale up deficiencies that have been described previously remain limiting.

Fuller et al. (IPN WO 01/92462 A1) presents a new bag that textures the surface of the gas permeable material in order to allow more surface area for gas transfer and cell attachment. However, medium height is also limited to that of the commercially available bags. That is because this bag is fabricated in the same manner as the other bags. Gas permeable surface area to medium volume ratio becomes even higher than that of other bags, and non-uniform medium distribution is present.

Basehowski et al. (U.S. Pat. No. 4,939,151) proposes a gas permeable bag that is suitable for adherent culture by making the bottom gas permeable, smooth, and charged for cell attachment. The inner surface of the top of the bag is textured to prevent it from sticking to the lower gas permeable surface. This bag only utilizes the lower surface for cell attachment, rendering it only as efficient in surface area to footprint ratio as a traditional flask.

To date, guidance is inadequate on how to create a device that eliminates the reliance on a gas/liquid interface and can integrate the scaffold of the multiple layer flasks without the need for perfusion. Static gas permeable devices only allow gas transfer through the bottom and top of the device. Thus, if traditional scaffolds are included, such as the styrene shelves provided in the multi-shelved tissue culture flasks, they will have the effect of inhibiting gas exchange at the cell location. Gas permeable materials should be located in a manner in which the attachment scaffold does not prevent adequate gas transfer. How that becomes beneficial will be further described in the detailed description of the invention herein.

The need to provide more efficient cell culture devices during scale up is not limited to static cell culture devices, but also applies to roller bottles. Traditional roller bottles function by use of a gas/liquid interface. The geometry is a clever way of providing more surface area and medium volume while occupying a smaller footprint than flasks and bags. Their universal use provides testimony to the market desire for devices that provide more efficient geometry, since that leads to reductions in the use of inventory space, incubator space, labor, and biohazardous disposal space.

When bottles are used for adherent culture, cells attach to the inner wall of the bottle. Cells obtain nutrients and gas exchange as the rolling bottle moves the attached cells periodically through the medium and gas space. Roller bottle use is not limited to adherent cells. They are also commonly used to culture suspension cells. For example, the culture of murine hybridomas for the production of monoclonal antibody is routinely done in roller bottles. In typical suspension cell culture applications, efficiency improvements related to footprint and size versus flasks can be attained, the handling simplicity of the roller bottle is superior to cell culture bags, and the low cost and level of complexity is superior to spinner flasks. Corning®, the leading supplier of roller bottles recommends medium volume for an 850 cm$^2$ bottle between 170 ml and 255 ml. The actual capacity of the bottle is about 2200 ml. Therefore, although the roller bottle provides advantages for both adherent and suspension cell culture, it is still very inefficient in geometry because the vast majority of the roller bottle, about 88%, is comprised of gas during the culture process. Roller bottles also deviate from the simplicity of static devices because ancillary roller mechanisms are required. Furthermore, they subject the cells to shear force. Those shear forces can damage or kill shear sensitive cells, and are not present in the traditional static devices.

McAleer et al. (U.S. Pat. No. 3,839,155) describes a roller bottle device configured to allow cells to attach to both sides of parallel discs oriented down the length of the bottle. Unlike the traditional bottle that rolls in the horizontal position, this device tumbles end over end to bring the discs through medium and then through gas. It does nothing to reduce the volume of gas residing in the bottle. On the contrary, it states "another advantage of the present invention is that extremely low volumes of fluid can be used." It relies entirely upon the presence of a large volume of gas, which must be perfused, in the bottle to function. The excessive volume of gas that hinders the efficient use of space in traditional bottles remains. Also, shear forces are not reduced.

Spielmann (U.S. Pat. No. 5,650,325) describes a roller bottle apparatus for providing an enhanced liquid/gas exchange surface. Trays are arranged in parallel within the bottle. The trays allow an increase of surface area for culture and are designed to allow liquid to flow over them as the bottle rotates. In the case of adherent cells, more surface area is available for attachment. In the case of suspension cells, they are stirred "in contact with gas and liquid phases" by the trays. Shear forces remain present. Although this apparatus provides an improved surface area, it relies entirely upon the presence of gas in the bottle to provide gas exchange. Thus, it does not address the fundamental limitation in space efficiency, which is the excessive volume of gas that must reside in the bottle.

If the roller bottle could be made to allow a vastly improved medium volume to gas ratio, it would provide a more economical option because the number of devices needed for scale up would be reduced. Since the typical medium volume for an 850 $cm^2$ bottle is 170 ml to 255 ml, but the capacity is 2200 ml, about a 9 to 13 fold increase in nutrient capacity could be made available by filling the bottle with medium. To retain simplicity, a non-complicated method of oxygenating the culture independent of a gas/liquid interface would need to exist. Also, for adherent culture, surface area should increase in proportion to the increase in medium volume. A gas permeable device with these characteristics could lead to a 9-fold to 13-fold reduction in the cost of sterilization, shipping, storage, use of incubator space, labor, and disposal cost. Shear forces on the cells could also be reduced.

For adherent culture, proposed and commercially available rolled gas permeable devices do not provide a superior alternative to traditional bottles because they have not integrated traditional attachment surfaces. Instead they rely upon small sections of attachment area or beads. Beads bring a new set of problems to those performing adherent culture. They are difficult to inoculate uniformly, it is not possible to assess cell confluence or morphology microscopically, and they must be separated from the cells that are attached to them if cell recovery is desired.

Attempts to eliminate the use of beads in gas permeable roller bottles have been made. Nagel et al. (U.S. Pat. No. 5,702,945), attempts to create the ability for the Falkenberg et al. devices to culture adherent cells without beads. One cell attachment matrix is provided in the cell culture compartment at the inner face of the gas membrane. Although adherent culture is possible, the bottle dimensions remain unchanged and, due to its small size, it fails to reduce the number of devices needed for scale up. Also, oxygen must transfer first through the gas permeable membrane and then through the cell attachment matrix to reach the cells. Furthermore, only one layer of cell attachment matrix is available, as opposed to the multiple layers of the NUNC™ Cell Factory and Corning CellStack™. Additionally, microscopic assessment of cell confluence and morphology is not accommodated.

An improved gas permeable roller bottle is needed. It should be capable of being filled with medium, used in standard roller racks, allowing an increase in cell attachment area in direct proportion to the increased medium volume, and retain the ease of use of the traditional bottle. It will be shown herein how this can be achieved.

Singh (U.S. Pat. No. 6,190,913) states that for "all devices that rely on gas-permeable surfaces, scale-up is limited". A bag is disclosed for resolving the scale up deficiencies of gas permeable devices. The non-gas permeable bag integrates medium and gas, in roughly equal proportions. The bag is placed on a rocker plate, and the rocking motion creates a wave in the medium, which enhances gas transfer. This patent covers the commercial product, available from Wave Biotech called the Wave Bioreactor. Unfortunately, custom rocking and temperature control equipment must be purchased for the apparatus to function, and the bag does not substantially alter the capacity to hold medium. As with gas permeable bags, the Wave Bioreactor bags are filled with medium to no more than one half of their carrying capacity. Thus, they limit medium height and inherit similar scale up deficiencies as gas permeable bags.

In summary, a need exists for improved cell culture devices and methods that bring more efficiency to research scale cell culture, and do not lose efficiency during scale up. Traditional devices that rely upon a gas/liquid interface to function are inefficient in terms of labor, sterilization cost, shipping cost, storage cost, use of incubator space, disposal cost, and contamination risk. Those devices include the petri dish, multiple well tissue culture plate, tissue culture flask, multiple shelved tissue culture flask, and roller bottle. Gas permeable devices are also inefficient, and in many cases lose the simplicity of the devices that require a gas/liquid interface to function. The petriPERM and Lumox multiwell plate gas permeable devices are in the form of their traditional counterparts, and inherit the inefficiencies of traditional devices. Gas permeable bags are inefficient due to medium height limitations, non-uniform medium distribution, use of high gas permeable material surface area to medium volume ratios, and the contamination risk present during feeding. Gas permeable cartridges are inefficient because they have a low height of medium, use a high gas permeable surface area to medium volume, house a small volume of medium, and require a very large number of units to be maintained during scale up. Rolled gas permeable devices are inefficient for scale up because they have geometry constraints that limit the distance that the walls can be separated from each other, require a large number of units during scale up due to limited medium volume, and often require custom rolling equipment. When adherent culture is desired, traditional devices have a very inefficient device volume to attachment surface area ratio, wasting space. Static, mixed, and rolled gas permeable devices become even more inefficient for adherent culture for reasons that include limited surface area, the use of beads for increased surface area, lack of traditional sheet styrene surfaces, and inability to perform microscopic evaluations.

Certain embodiments disclosed herein provide more efficient cell culture devices and methods, that overcome the limitations of prior devices and methods, by creating gas permeable devices that can integrate a variety of novel attributes. These various attributes include gas exchange without reliance upon a gas/liquid interface, increased medium height, reduced gas permeable surface area to medium volume ratios, gas exchange through the device side walls, cell support scaffolds that are comprised of traditional materials, and increased gas permeable material thickness.

SUMMARY OF THE INVENTION

It has been discovered that for gas permeable devices comprised of a lower gas permeable material, it can be beneficial to increase medium height beyond that dictated by conventional wisdom or allowed in commercially available devices. It is contemplated by the inventors hereof that convection of substrates within cell culture medium plays a more important role than previously recognized. It would appear that the historic reliance upon diffusion for mass transfer underestimates the contribution that convection makes. That would result in underestimating the rate of travel of substrates such as glucose and lactate in cell culture medium, and a failure to recognize that medium residing farther away from cells than traditionally allowed can be useful to the cells. If the rate of travel of substrates in medium were underestimated, medium residing in areas believed to be too far away from the cells would incorrectly deemed to be wasted. The logical consequence would be to unnecessarily configure the gas permeable device to hold less medium than could be useful to the cells, in order to reduce the space occupied by the device, making it more economically sterilized, shipped, stored, and disposed of.

In any event, and as an example of how medium residing at a distance beyond conventional wisdom can be beneficial, tests were conducted in which medium height was increased far beyond that suggested previously, or even possible in commercially available static gas permeable devices. Evaluations of a common cell culture application, using murine hybridomas, demonstrated that more cells were able to reside in a given footprint of the device by increasing medium height relative to conventional wisdom. This benefit, not previously recognized, allows a variety of cell culture device configurations that provide more efficient cell culture and process scale up to become available.

The inventive apparatus and methods herein demonstrate that the gas/liquid interface is not necessary for adequate gas exchange when a wall of a device is gas permeable, scaffolds are present, and the device is operated in a static mode. This eliminates the need for excess device size that results from the presence of gas in traditional devices, and allows gas permeable devices to integrate traditional scaffolds. This allows a variety of cell culture device configurations that occupy less space than prior devices, and makes them more efficient for scale up. Again, it is contemplated by the inventors that the role of convection may be a contributing factor.

It has also been discovered that geometric configurations for gas permeable roller bottles, that contradict the guidance of conventional wisdom, can successfully culture cells. The new geometry allows the device to contain more medium than previously possible, thereby yielding a geometric shape that improves scale up efficiency. This allows cell culture device configurations to exist that eliminate the wasted space of traditional bottles that contain gas for oxygenation, and are superior to gas permeable bottles in terms of scale up efficiency.

It has also been discovered that cells can be effectively cultured using silicone gas permeable material that is thicker than conventional wisdom advocates.

These discoveries have made it possible to create new devices and methods for culturing cells that can provide dramatic efficiency and scale up improvements over current devices such as the petri dish, multiple well tissue culture plate, tissue culture flask, multiple shelved tissue culture flask, roller bottle, gas permeable petri dish, gas permeable multiple well plate, gas permeable cell culture bag, compartmentalized gas permeable devices, and gas permeable rolled devices.

Certain embodiments disclosed herein provide superior gas permeable cell culture devices, by increasing wall height in order to allow increased medium heights and reduced gas permeable surface area to medium volume ratios.

Certain embodiments disclosed herein provide superior cell culture methods using gas permeable cell culture devices, by increasing medium heights and reducing gas permeable surface area to medium volume ratios.

Certain embodiments disclosed herein provide superior cell culture devices, by allowing gas exchange through a sidewall at least partially comprised of gas permeable material.

Certain embodiments disclosed herein provide superior cell culture methods using gas permeable devices, by allowing gas exchange through a sidewall at least partially comprised of gas permeable material.

Certain embodiments disclosed herein provide a superior alternative to gas permeable multiple well tissue culture plates, by increasing wall height in order to allow increased medium height and reduced gas permeable surface area to medium volume ratios.

Certain embodiments disclosed herein provide a superior alternative to gas permeable petri dishes, by increasing wall height in order to allow increased medium height and reduced gas permeable surface area to medium volume ratios.

Certain embodiments disclosed herein provide a superior alternative to the method of cell culture in gas permeable cell culture bags, by increasing medium height in order to provide more nutrient support and reducing gas permeable surface area to medium volume ratios.

Certain embodiments disclosed herein provide a superior alternative to the gas permeable cartridges, by increasing wall height in order to allow increased medium heights and reduced gas permeable surface area to medium volume ratios.

Certain embodiments disclosed herein provide a superior alternative to the gas permeable roller bottles, by creating a geometry that allows medium to reside at a distance from the gas permeable material beyond that previously possible.

Certain embodiments disclosed herein provide superior gas permeable cell culture devices that can be operated in the horizontal and vertical position.

Certain embodiments disclosed herein provide a superior alternative to the compartmentalized gas permeable devices, by increasing wall height in order to allow increased medium heights and reducing gas permeable surface area to medium volume ratios.

Certain embodiments disclosed herein provide a superior cell culture methods using compartmentalized gas permeable devices, by increasing medium height and reducing gas permeable surface area to medium volume ratios.

Certain embodiments disclosed herein provide superior gas permeable cell culture devices that utilize silicone material for gas exchange, by configuring them with silicone that is greater than 0.005 inches thick.

Certain embodiments disclosed herein provide an improved cell culture bag in which the gas permeable material is silicone that exceeds 0.005 inches thick.

BRIEF DESCRIPTION OF THE DRAWINGS

FIG. 1A shows FIG. 2, and FIG. 1B shows FIG. 3, of this Jensen et al. paper in which Dcm is the diffusion constant of medium and the model for steady state values of PO2 and PCO2 are shown in a gas permeable container.

FIG. 4A is an embodiment of a cell culture device with a housing comprised of a lower gas permeable material, configured to allow a large volume of medium to reside above its lower gas permeable material. A removable lid protects it from contaminants. FIG. 4B is an embodiment of a cell culture device with a housing comprised of a lower gas permeable material, configured to allow a large volume of medium to reside above its lower gas permeable material. The container is accessible by septum. FIG. 4C is an embodiment of a cell culture device with the walls comprised of gas permeable material such that the device can be laid on its side and operated in the non-rolling or rolling position.

FIG. 17 is a cross-sectional view of a test fixture used to assess the ability to culture adherent cells in the absence of a gas/liquid interface by allowing gas transfer through a sidewall of the test fixture. Biological evaluations using this test fixture demonstrated the ability to culture cells in the absence of a gas/liquid interface. These surprising results allow device configurations not previously contemplated to exist.

FIG. 18 is a cross-sectional view of a test fixture used to assess the ability to culture adherent cells in the absence of a gas/liquid interface by allowing gas transfer through a sidewall of the test fixture. Multiple scaffolds were integrated into the test fixture. Biological evaluations using this test fixture demonstrated the ability to culture cells in the absence of a gas/liquid interface. These surprising results allow device configurations not previously contemplated to exist.

DETAILED DESCRIPTION OF THE INVENTION

Figure 1A:
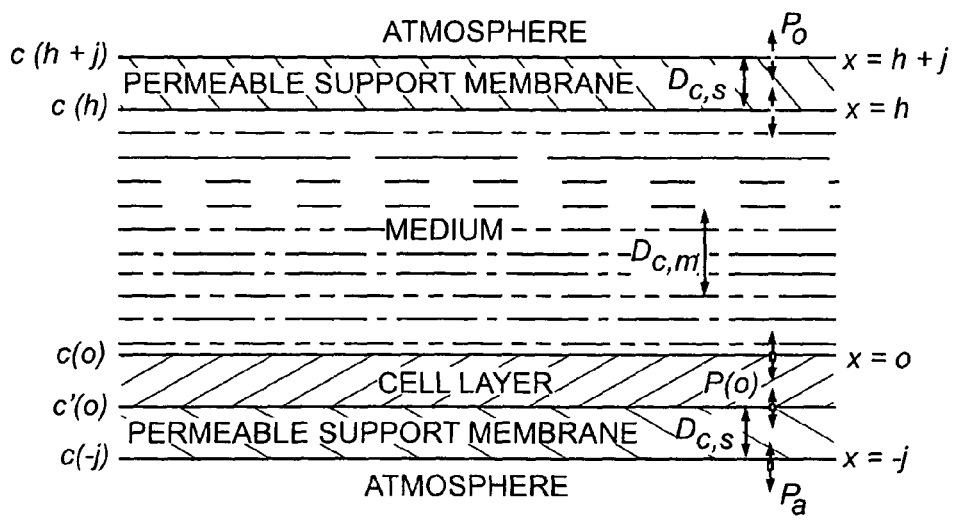
FIG. 1A and FIG. 1B are obtained from Jensen et al., "Diffusion in Tissue Cultures on Gas-permeable and Impermeable Supports", J. Theor. Biol. 56, 443-458 (1976)
Figure 1B:
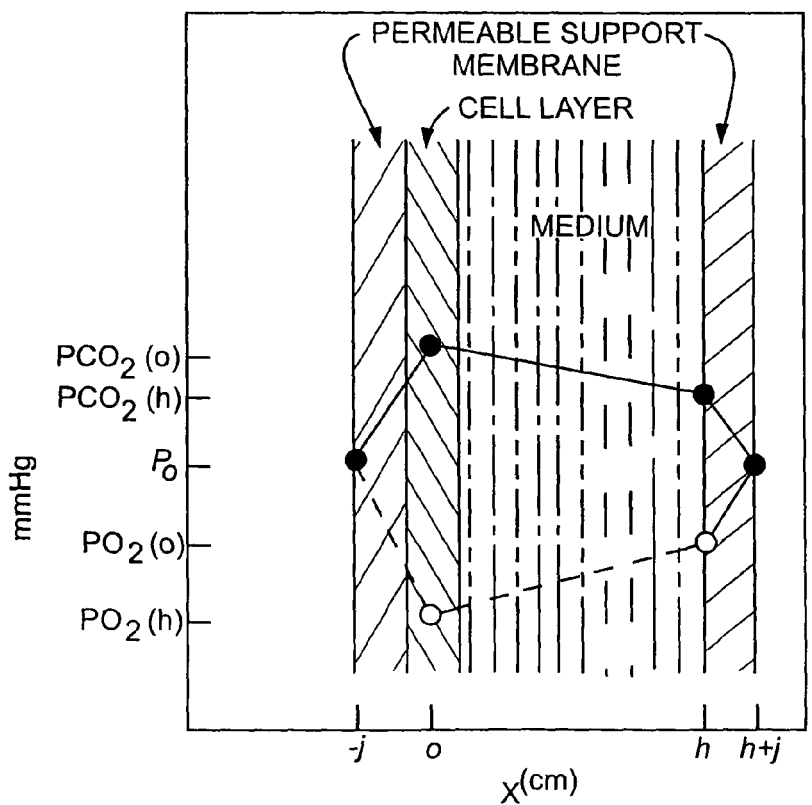
Figure 2:
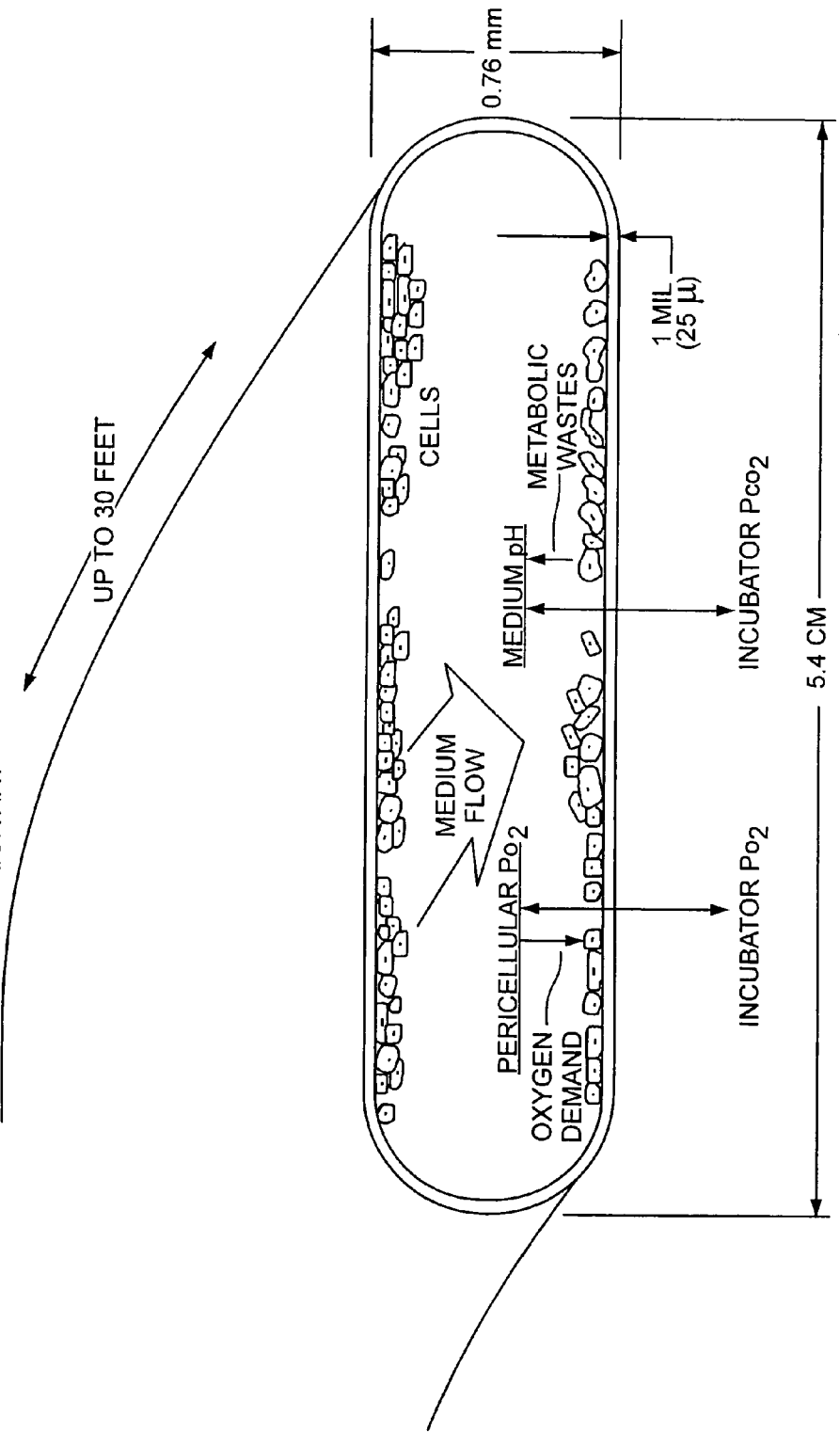
FIG. 2 is a copy of FIG. 2 from Jensen, "Mass cell culture in a controlled environment", Cell Culture and its Applications, Academic Press 1977, showing a gas permeable cell culture device configured with a low medium height capacity.
Figure 3:
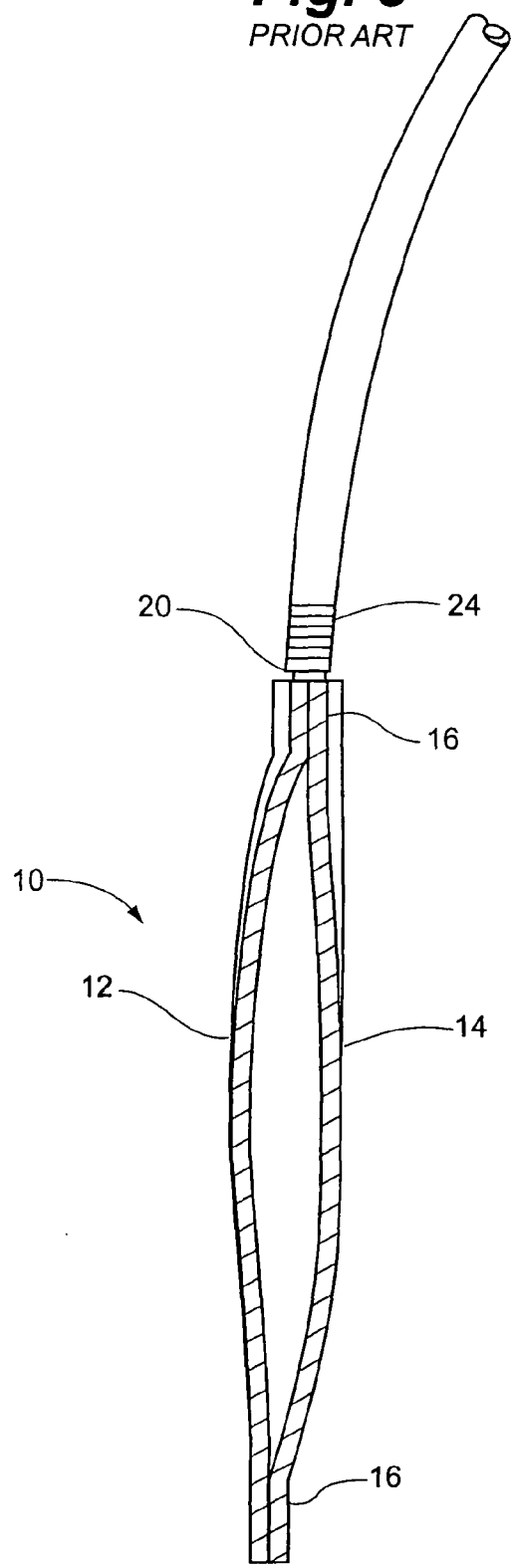
FIG. 3 is a copy of FIG. 2 of U.S. Pat. No. 5,686,304, which has been commercialized as the Si-Culture™ bag (Medtronic Inc.), showing a typical cell culture bag cross-section.

By configuring gas permeable devices to be capable of holding medium at a height not contemplated in prior cell culture devices or methods, advantages can accrue including reduced handling frequency, labor, sterilization cost, shipping cost, storage cost, use of incubator space, disposal cost, and contamination risk. Reducing the ratio of gas permeable surface area to medium volume to a ratio not contemplated in prior cell culture devices or methods can also increase culture efficiency. It allows an increase in medium height without a corresponding increase in device length or width. In the preferred embodiments, provisions are made that allow either medium height to increase or the ratio of gas permeable surface area to medium volume to decrease. Provisions can also be made that allow both the medium height to increase and the ratio of gas permeable surface area to medium volume to decrease.

A wide variety of embodiments for gas permeable devices and methods that allow medium to reside at heights beyond conventional wisdom are possible. They can take the form of prior devices, or entirely new forms. If the form is a gas permeable petri dish up to 50 mm in diameter, medium height should preferably exceed 0.36 cm. A preferred wall height is in excess of 6 mm. If the form is a gas permeable petri dish greater than 50 mm in diameter, medium height should preferably exceed 0.51 cm. A preferred wall height is in excess of 12 mm. If the form is a multiple well tissue culture plate with 384 wells or more, medium height should preferably exceed 0.91 cm and preferred well depth is in excess of 11.5 mm; greater than 24 wells to less than 384 wells, medium height should preferably exceed 0.97 cm and preferred well depth is in excess of 10.9 mm; 24 wells or less, medium height should preferably exceed 1.03 cm and preferred well depth is in excess of 16.5 mm. If the form is a gas permeable cartridge, medium height and wall height should preferably be greater than 1.27 cm. If in the form of a cell culture bag, medium height should preferably reside beyond 2.0 cm in height at the highest point. If the form is a compartmentalized device, and all medium in the device resides entirely above the semi-permeable membrane, medium height in the nutrient compartment should preferably reside beyond 1.0 cm in height above the semi-permeable membrane. If the form is a compartmentalized gas permeable device, medium height in the nutrient compartment should preferably reside beyond 5.2 cm in height above the semi-permeable membrane.

If it is the design objective to reduce the gas permeable surface area to medium volume ratio relative to conventional wisdom, a wide variety of embodiments for gas permeable devices and methods are possible. They can take the form of prior devices, or entirely new forms. If the form is a gas permeable petri dish below 50 mm in diameter, the gas permeable surface area to medium volume ratio should preferably be below 2.74 $cm^2$/ml. If the form is a gas permeable petri dish 50 mm or greater in diameter, the gas permeable surface area to medium volume ratio should preferably be below 1.96 $cm^2$/ml. If the form is a multiple well tissue culture plate with 384 wells or more, the gas permeable surface area to medium volume ratio should preferably be below 1.10 $cm^2$/ml; less than 24 wells to less than 384 wells, the gas permeable surface area to medium volume ratio should preferably be below 1.03 $cm^2$/ml; 24 wells or less, the gas permeable surface area to medium volume ratio should preferably be below 0.97 $cm^2$/ml. If the form is a gas permeable cartridge in which two sides of the cartridge are gas permeable, the surface area to medium volume ratio should preferably be below 0.79 $cm^2$/ml. If in the form of a cell culture bag, the gas permeable surface area to medium volume ratio should preferably be below 1.0 $cm^2$/ml. If the form is a compartmentalized device, and all medium in the device resides entirely above the semi-permeable membrane, the gas permeable surface area to medium volume ratio should preferably be below 1.74 $cm^2$/ml. If the form is a compartmentalized device, and all medium in the device does not reside entirely above the semi-permeable membrane, the gas permeable surface area to medium volume ratio should preferably be below 0.31 $cm^2$/ml.

FIG. 4A shows a cross-sectional view of one embodiment of the invention. Gas permeable cell culture device 10 is configured to allow cells 20 to reside upon lower gas permeable material 30. Although FIG. 4A shows gas permeable cell culture device 10 structured in the style of a petri dish, any number of shapes and sizes are possible that allow medium to reside at a height beyond that of conventional wisdom.

Top cover 55 can be removed to allow medium 50 to be conveniently added and removed, by either pouring or pipetting, to and from gas permeable cell culture device 10. However, access for medium 50 can also be made in any number of ways common to cell culture devices, including by way of caps, septums, and tubes. In the event that a closed system is desired, gas permeable cell culture device 10 can be configured with inlet and outlet tubes that can be connected to medium source and waste bags by way of a sterile tubing connection, using equipment such as that made by Terumo Medical Corp. (Somerset, N.J.). Septum configurations, or any other techniques known to those skilled in the art, can also be used to create a closed container. For example, as shown in FIG. 4B, gas permeable cell culture device 10 can be alternatively configured as a closed container with septums 65.

In the event that gas permeable cell culture device 10 is to be completely filled with medium 50, and cells are intended to settle out of medium 50 by gravity, the profile of the top of gas permeable cell culture device 10 preferably allows medium 50 to reside at a uniform height above gas permeable material 30. This will allow uniform deposit of cells onto lower gas permeable material 30, when cells gravitationally settle from suspension within medium 50. The configuration of FIG. 4B achieves this purpose.

The lower gas permeable material, e.g., material 30, can be any membrane, film, or material used for gas permeable cell culture devices, such as silicone, flouroethylenepolypropylene, polyolefin, and ethylene vinyl acetate copolymer. A wide range of sources for learning about gas permeable materials and their use in cell culture can be used for additional guidance, including co-pending U.S. patent application Ser. No. 10/460,850 incorporated herein in its entirety. The use of the words film and membrane imply a very thin distance across the gas permeable material, and the inventors have found that the embodiments of this invention function when the gas permeable material of the described devices and methods is beyond the thickness associated with films and membranes. Therefore, the portion of the device that contributes to gas exchange of the culture is called a gas permeable material herein.

Those skilled in the art will recognize that the gas permeable material should be selected based on a variety of characteristics including gas permeability, moisture vapor transmission, capacity to be altered for desired cell interaction with cells, optical clarity, physical strength, and the like. A wide variety of information exists that describe the types of gas permeable materials that have been successfully used for cell culture. Silicone is often a good choice. It has excellent oxygen permeability, can allow optical observation, is not easily punctured, typically does not bind the cells to it, and can be easily fabricated into a wide variety of shapes. If silicone is used, it may be less than about 0.2 inches, about 0.1 inches, about 0.05 inches, or about 0.030 inches in the areas where gas transfer is desired. The best selection of material depends on the application. For example, Teflon® may be preferred in applications that will be exposed to cryopreservation. For adherent culture, in which cells are to attach to the gas permeable material, WO 01/92462, U.S. Pat. Nos. 4,939, 151, 6,297,046, and U.S. patent application Ser. No. 10/183, 132 are among the many sources of information that provide guidance.

If silicone is used as a gas permeable material, increasing thickness beyond conventional wisdom may expand the options for design, cost reduce the manufacturing process, and minimize the possibility of puncture. For example, molding a part with a large surface area when the part must be very thin can be difficult because material may not flow into the very small gap between the core and the body of the mold. Thickening the part, which widens that gap, can make the molding process easier. In additional to possible molding advantages, thicker gas permeable materials also are less likely to puncture or exhibit pinholes.

The height of walls, e.g., walls 40, plays an important role in device scale up efficiency. Prior static gas permeable devices limit medium height. For example, bags provide no walls and instructions limit medium height, while cartridge style devices only provide a very low wall height (e.g. Opticell® cartridges, CLINIcell® Culture Cassettes, and Petaka™ cartridges). An object of this invention is to provide for increased medium height, thereby increasing device efficiency. The height of the walls can dictate how much medium is allowed to reside in the device. Adding medium provides a larger source of substrates, and a larger sink for waste products. By increasing wall height when more medium is needed during scale up, the geometry of the device is more compatible with the shape of incubators, flow hoods, and biohazard disposal bags. Furthermore, the increase in volume relative to the surface area upon which cells reside can allow more medium per cell to be present. That can have the effect of reducing feeding frequency, thereby reducing labor and contamination risk. It can also have the effect of increasing the number of cells residing per square centimeter of device footprint.

Structuring walls to allow an increase in medium volume can also have the beneficial effect of diminishing the effects of medium evaporation. Medium evaporation is a problem in cell culture because it alters the concentration of solutes residing in the medium. Existing gas permeable devices are prone to such an event because they have a high gas permeable surface area to medium volume ratio. Attempts to prevent such an event are described in U.S. patent application Ser. No. 10/216,554 and U.S. Pat. No. 5,693,537 for example. However, simply allowing an increase in the volume of medium in the device can reduce the impact of evaporation. If prior static gas permeable devices allowed an increase in medium volume to gas permeable surface area ratio, the rate of solute concentration change when evaporation is present would be reduced proportionally.

In a preferred embodiment, walls should be capable of allowing medium to reside at a height that exceeds that of devices that rely upon a gas/liquid interface and more preferably exceeds that of typical static gas permeable devices. For example, the height of wall 40 is beyond 3 mm, and more preferably beyond 2.0 cm, and will thus provide advantages. By providing users of the device the option of adding more medium to the device than prior gas permeable devices, many advantages accrue including the ability to house more cells per device, feed the device less frequently, and scale the device up without increasing the footprint. Walls can be comprised of any biocompatible material and should mate to lower gas permeable material in a manner that forms a liquid tight seal. The methods of mating a lower gas permeable material to walls include adhesive bonding, heat sealing, compression squeeze, and any other method commonly used for generating seals between parts. As an option, walls and lower gas permeable material can be formed of the same material and fabricated as a single entity. For example, if silicone is used, walls and the lower gas permeable material could be liquid injection molded, or dip molded, into a single gas permeable piece. That has the advantage of creating a gas permeable surface for cells to reside upon when a gas permeable cell culture device is stood vertically as shown in FIG. 4B, or laid on its side as shown in FIG. 4C, which shows gas permeable wall 41 with cells 20 resting thereupon.

Laying certain gas permeable cell culture devices on a side can help make optimal use of incubator space as the profile of the device can be reduced when it is too tall for narrowly spaced incubator shelves. In the case where it is desirable to have the gas permeable cell culture device reside on its side, making the device square or rectangular, instead of circular, will create a flat surface for cells to reside on when on its side. That is advantageous as it prevents localized areas for cells to pile upon each other, potentially causing harmful gradients. In the case where the device depth and width differ in dimension, three alternate surface areas are available for cells to reside upon, and three alternative maximum medium heights exist, depending on the position gas permeable cell culture device is placed in. When the device is structured for operation in these alternate positions, the surface upon which the device resides is preferably comprised of gas permeable material. That allows cells that settle by gravity onto this surface to be at optimal proximity for gas exchange.

Walls are preferably configured with enough structural strength that medium is retained in a relatively symmetrical shape above gas permeable material in order to make most efficient use of lab space, minimize gradient formation within a medium, and allow a uniform deposit of cells upon a lower gas permeable material during inoculation. It is also advantageous if walls allow visual assessment of color changes in medium in order to determine pH or contamination status. Walls may be configured in a manner that allows a gas permeable cell culture device to be easily lifted by hand. When it is desirable for walls to be gas permeable, and if a separate entity is placed around walls to retain them in a rigid position, it preferably should not block gas contact with the majority of walls.

Gas permeable cell culture devices can be configured to function either in the static or rolled mode. To do so, gas permeable cell culture devices should preferably be cylindrical. A cylindrically shaped body provides more volume than a square or rectangular body when the device is to be placed in a standard roller rack. However, a non-cylindrical body shape can still function on a roller rack by attaching a circular housing around the body. If it is desired to provide users with the option of device functioning in the vertical, horizontal, or rolling position, both the bottom and the sidewalls of the gas permeable cell culture device should be comprised of gas permeable material. If the device is only to be operated in the horizontal, rolled or unrolled, position, it may be more cost effective and minimize surface area for evaporation if the ends of the device are not comprised of gas permeable material.

If a gas permeable cell culture device is configured in a cylindrical shape with a lower gas permeable material, and the walls are comprised of gas permeable material, it can be stood vertically or rolled depending on user preference. It can be advantageous to roll gas permeable cell culture device when maximum mixing will benefit an application, such as can be the case when seeking to decrease antibody production time. If this option is desired, the walls of gas permeable cell culture device should be made gas permeable in the same manner described for lower gas permeable material. Although there are no restrictions on bottle length or diameter, it can be advantageous if the walls conform to the diameter of standard roller bottles so that gas permeable cell culture device can function on a standard roller rack.

If it is desirable to reduce cell shear, filling the device entirely with medium will eliminate gas from the device so that it cannot contribute to cell shear. The ports can be designed in any number of ways that reduce the risk of contamination as medium fills the device entirely. Also, when the device is to be rolled or function on its side, only side surfaces need be comprised of gas permeable material.

The scale up advantages provided by a device that allows medium to reside at a height that exceeds conventional wisdom will become apparent to those skilled in the art, in light of the Examples demonstrating biological outcomes herein. As an example of scale up efficiency, when a gas permeable cell culture device is cylindrical, operated in the vertical position, and the bottom provides for gas exchange, doubling the diameter increases the volume by a factor of four when the height is held constant. For example, a device of approximately 4.5 inches in diameter and about 7.7 inches tall, will house about 2 L of medium. By making the device 9.0 inches in diameter, it will house 8 L of medium. By making the device 18.0 inches in diameter, it will house 32 L of medium. Thus, culture volume can easily be scaled up while holding key parameters constant, such as the medium height and gas permeable surface area to medium volume ratio. By holding these parameters constant, protocols that are developed in a small volume device are likely to remain unchanged as device volume increases.

Figure 5:
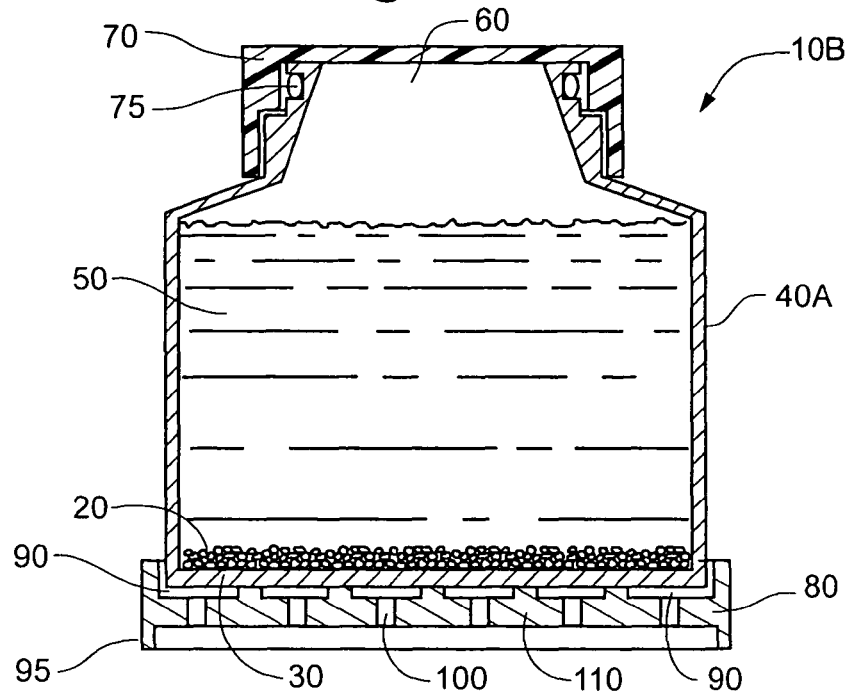
FIG. 5 is an embodiment of a gas permeable cell culture device with a lower gas permeable material configured to allow cells to distribute evenly about its lower surface and provide gas to the underside of the lower gas permeable material.

When a gas permeable cell culture device is operated in the vertical position, and suspension cells are being cultured, it is beneficial if ambient gas can make relatively unobstructed contact with the underside of the lower gas permeable material. For example, in incubators in which the shelves are non perforated, gas transfer in and out of the culture can be limited if the lower gas permeable material makes contact with the incubator shelf. In the embodiment shown in the cross-sectional view of FIG. 5, lower gas permeable material support 80 acts to ensure that lower gas permeable material 30 is in contact with ambient gas by maintaining a gas compartment 90. In the preferred embodiment, gas compartment 90 is maintained by allowing lower gas permeable material support 80 to make partial contact with lower gas permeable material 30 in a manner that does not diminish the amount of gas exchange required to support the culture. In addition to allowing exposure to ambient gas, lower gas permeable material support 80 maintains lower gas permeable material 30 in a substantially horizontal state such that cells 20 do not pile up in any low points. That would cause diffusional gradients and limit cell growth relative to a condition in which cells 20 could distribute evenly across lower gas permeable material 30. Therefore, a design objective for lower gas permeable material support 80 may be to contact lower gas permeable material 30 in as many locations as needed to keep it substantially horizontal while still allowing adequate gas contact with the lower surface of lower gas permeable material 30. Those skilled in the art will recognize there are many ways to achieve this objective. As shown in FIG. 5, projections 110 achieve this objective.

A "bed of nails" configuration is one way to maintain lower gas permeable material 30 in a substantially horizontal position while allowing adequate gas exchange. For example, 1 mm×1 mm squares, distributed evenly and projecting 1 mm from the lower gas permeable material support can retain the lower gas permeable material in a substantially horizontal position. When the projections 110 occupied 50% of the surface of lower gas permeable material support 80 as shown in FIG. 5, this configuration allowed adequate gas exchange to culture about 10 to 15 million murine hybridoma cells per square centimeter on a silicone membrane of about 0.004 inches thick. As also shown in FIG. 5, lower gas access openings 100 allow gas to enter and exit gas compartment 90 of lower gas permeable material support 80 by passive diffusion. This allows gas permeable cell culture device 10B to function in ambient conditions without need of ancillary pumping mechanisms. Feet 95 elevate lower gas permeable material support 80, allowing ambient gas to be available to lower gas access openings 100. This information also is applicable to maintaining a gas compartment around sidewalls when the device functions as described on its side in either the rolling or non-rolling mode. Other possibilities of allowing adequate gas access to a gas permeable material can be utilized. For example, the CELLine™ products from Integra Biosciences AG utilize open mesh elevated from a lower plastic support by feet to allow gas access to the gas permeable membrane. U.S. Pat. No. 5,693,537 also provides additional guidance for this feature.

In the configuration shown in FIG. 5, cap 70 covers medium access port 60 to prevent contamination. O-ring 75 ensures that medium 50 will not leak from gas permeable cell culture device 10B, such as when it is in the horizontal position, completely filled, or accidentally dropped.

Figure 6:
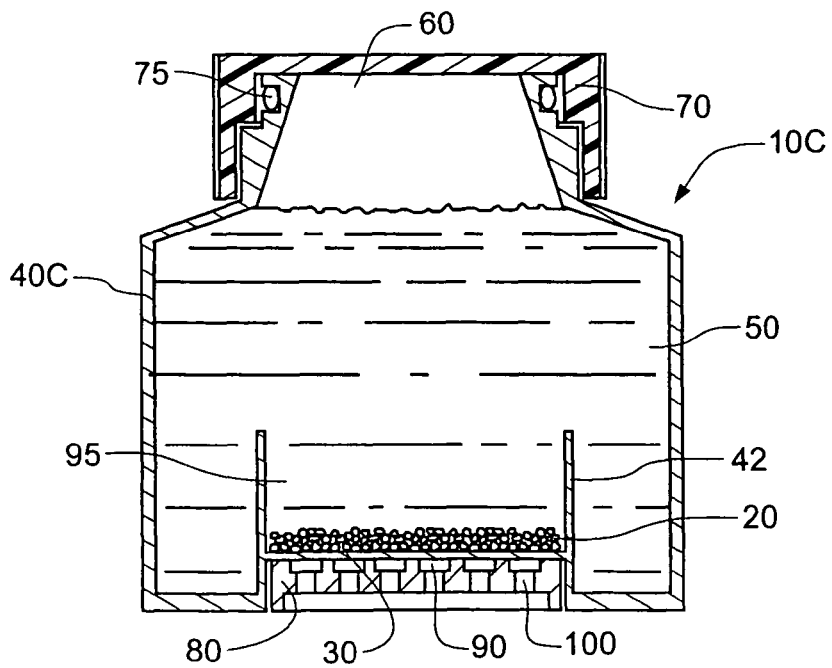
FIG. 6 is an embodiment of a gas permeable cell culture device configured to maintain medium in areas not directly above the cells being cultured, in order to provide additional nutrient support without a further increase in device profile.

In certain embodiments, the medium does not need to reside entirely above the lower gas permeable material. A portion of the medium can reside in areas not directly above a lower gas permeable material in order to reduce the profile of a vertical cell culture device, which may be desirable for use in incubators with limited distance between shelves. The cross-sectional view of FIG. 6 shows an embodiment configured for suspension cell culture in which walls 40C are offset from lower gas permeable material 30 in order to decrease the profile of gas permeable cell culture device 10C when operated in the vertical position. In this configuration, the ratio of medium volume to surface area upon which cells reside can be held constant while the profile of the device is reduced in size by simply increasing the width, or diameter, of gas permeable cell culture device 10C. Care should be taken to ensure that cells 20 continue to reside above lower gas permeable material 30 during inoculation, feeding, and handling. Interior walls 42 achieve this by allowing gravity to keep cells 20 in the area above lower gas permeable material 30. In a preferred embodiment, the walls should be capable of allowing medium to reside at a height above lower gas permeable material 30 that exceeds 3 mm.

Figure 7A:
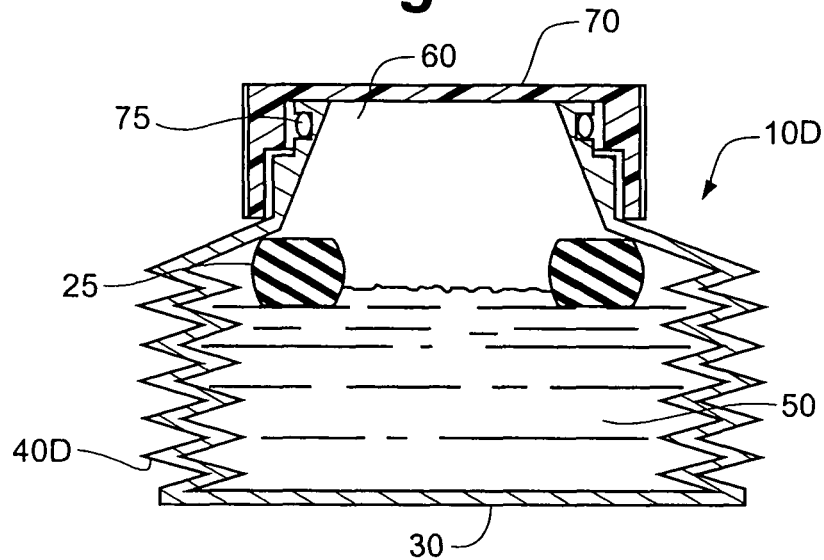
FIG. 7A and FIG. 7B are two views of an embodiment of a gas permeable cell culture device configured so that it can adjust in height as the volume of medium within it changes, thereby occupying as little space as possible at each stage of the culture process and allowing the capability of being sterilized, shipped, stored, and disposed of in a minimum volume condition which reduces the cost of the process.
Figure 7B:
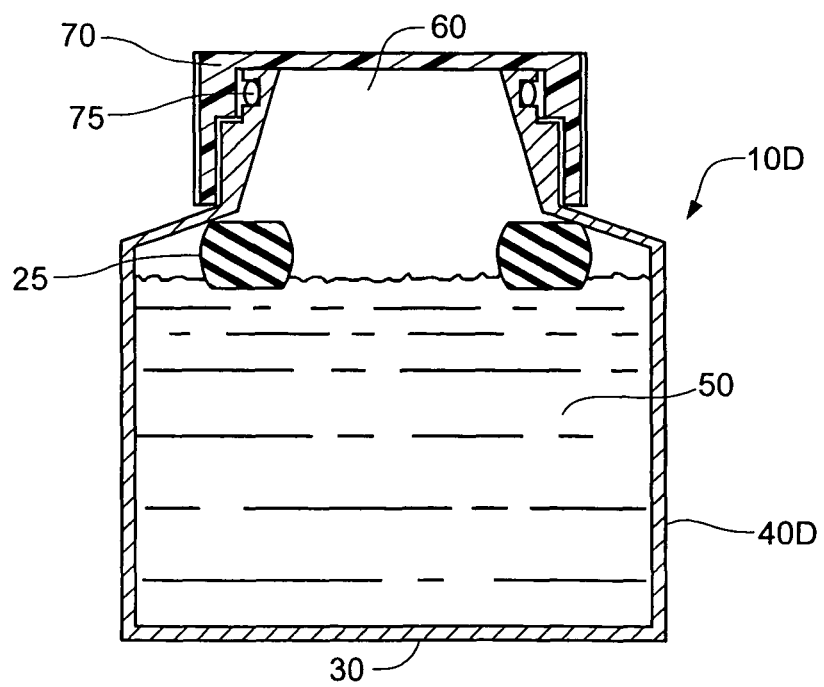

FIG. 7A and FIG. 7B show cross-sectional views of a preferred embodiment for a gas permeable cell culture device that can raise or lower its height in response to the volume of medium residing within it. In FIG. 7A, medium 50 is added to gas permeable cell culture device 10D and makes contact with buoyant shoulder 25. In FIG. 7B, medium 50 exerts an upward force on buoyant shoulder 25, causing gas permeable cell culture device 10D to rise in height in response to the increasing volume of medium 50. In the configuration shown, walls 40D are bellows shaped to allow extension and contraction of the height of gas permeable cell culture device 10D. Buoyant shoulder 25 can be any biocompatible material that is less dense than medium 50. It can also be an integral part of walls 40. It should be sized to displace the appropriate volume of medium 50 in order to exert enough force to extend gas permeable cell culture device 10D upward. In this configuration, gas permeable cell culture device 10D only occupies as much space as needed to perform the culture and one product can be the optimal size for a variety of applications. For example, the volume of medium suitable for culturing hybridomas may differ from the amount of medium suitable for maintaining pancreatic islets. In that case, gas permeable cell culture device 10D only need occupy as much space as needed for each application. Also, it allows sterilizing, shipping, storage, incubation, and disposal in the minimum volume condition, thereby reducing the cost of the culture process. Those skilled in the art will recognize that there are many other ways of altering the device profile other than buoyancy, including a wide variety of mechanical mechanisms such as those described in co-pending U.S. patent application Ser. No. 10/460,850.

Figure 8:
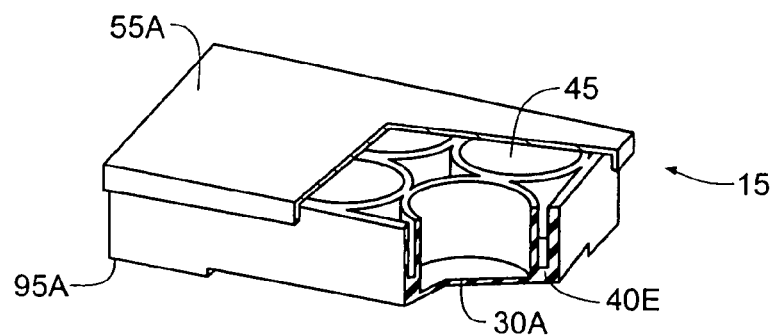
FIG. 8 is an embodiment of a gas permeable cell culture device configured in a multiple well format, capable of holding an increased volume of medium per well relative to traditional multiple well tissue culture devices, thereby allowing more efficient research scale culture by increasing the amount of cells present per well, reducing feeding frequency, and allowing better clone selection possibilities.

FIG. 8 shows an embodiment for a gas permeable multiple well plate 15, in which the bottom of each well is gas permeable. The properties of lower gas permeable material 30A are the same as those described in the embodiment of FIG. 4A. Although a six well plate is shown, any number of individual wells 45 can be present, including the traditional formats of six, twenty-four, forty-eight, and ninety-six wells. Walls 40E are structured to allow medium to reside at a height above lower gas permeable material 30A that exceeds the wall height of traditional multiple well plates, thereby increasing the number of cells that can reside in each well while reducing the footprint relative to traditional multiple well plates. For example, murine hybridoma cells typically can reside at a density of $1 \times 10^6$ cells per ml of medium. When the well has a diameter of 8.6 mm, and 2 mm of medium height, 0.12 ml of medium is present and about $0.12 \times 10^6$ cells can reside per well. However, if 1 ml of medium could reside in the well by making the wall taller, enough medium to support nearly five times as many cells (i.e. $1 \times 10^6$ cells per ml) could be present per well, provided that number of cells could reside upon a gas permeable material with a surface area of 0.58 $cm^2$ (i.e. 8.6 mm diameter). Example 1 demonstrates that many more than $1 \times 10^6$ murine hybridoma cells can reside on a surface area this size depending on medium volume. Not only can more medium support more cells, it can allow feeding frequency to be reduced, and reduce the rate at which evaporation alters medium composition.

Walls can be comprised of any biocompatible material and should mate to the lower gas permeable material in a manner that forms a liquid tight seal. The methods of mating lower gas permeable material 30A to walls 40E are the same as those described for the embodiment of FIG. 4A. Also, as described in the embodiment of FIG. 4A, walls 40E and lower gas permeable material 30A can be formed of the same material and fabricated as a single entity. Lower gas permeable material 30A can be supported in a substantially horizontal position as shown in FIG. 5, where lower gas permeable material support 80 is configured with lower gas access openings 100 in communication with gas compartment 90. In the event that the span of the bottom of well 45 is small, support may be unnecessary because the physical strength of lower gas permeable material 30A can retain it in an adequate horizontal position, depending on the thickness and physical properties of the gas permeable material. In this case, feet 95A can be used to elevate gas permeable multiple well plate 15 so that gas transfer is not a problem in an incubator with non-perforated shelves. Top cover 55A prevents contamination and minimizes evaporation.

Figure 9A:
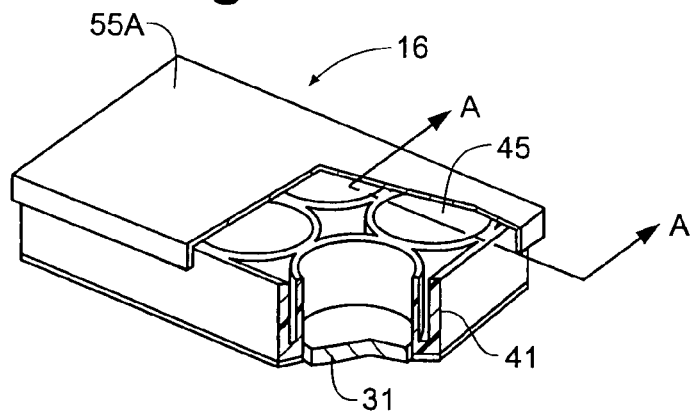
FIG. 9A and FIG. 9B are views of embodiments of a gas permeable cell culture device in a multiple well format, configured with a gas permeable sidewall. The lower surface of each well of the device can be comprised of exactly the same material as traditional tissue culture flasks. Elimination of the gas/liquid interface as a requirement for gas exchange allows for an increased number of cells per well and/or reduced frequency of feeding, better use of incubator space, as well as cost reductions in sterilization, shipping, storage, and disposal.
Figure 9B:
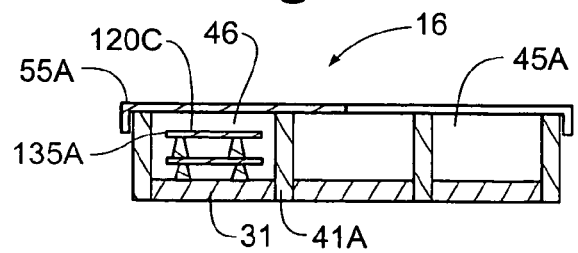

FIG. 9A shows a cutaway of a perspective view, and well 45A of FIG. 9B shows cross-section A-A, of a preferred embodiment for a gas permeable multiple well plate 16. In this embodiment, the walls of the wells are gas permeable. Although a six well plate is shown, any number of individual wells 45A can be present, including the traditional formats of six, twenty-four, forty-eight, and ninety-six wells. This configuration may be useful when it is desirable to retain either the microscopic, attachment surface, or light visibility properties of the traditional multiple well tissue culture plate. Yet, by making each well 45A deeper than the maximum depth of traditional multiple well plates used for cell culture, more medium can be made available for culture and the gas permeable nature of the walls will allow proper gas exchange of the culture, rendering the location of the gas/liquid interface inconsequential. Non-gas permeable bottom 31 mates to gas permeable wall 41 in a liquid tight manner. There are a number of ways to achieve this objective. For example, the diameter of non gas permeable bottom 31 can slightly exceed the diameter of gas permeable wall 41, causing gas permeable wall 41 to apply a force against non gas permeable bottom 31, thereby creating a liquid tight seal. Gas permeable wall 41 can have any of the properties as described for the gas permeable material of FIG. 4A. However, in a preferred embodiment gas permeable wall 41 is comprised of silicone because of its ability to be easily fabricated by liquid injection molding, and its capacity to stretch and provide a liquid tight seal against non-gas permeable bottom 31. Non-gas permeable bottom 31 can be any plastic commonly used in traditional multiple well tissue culture plates, or any other cell attachment material known to those skilled in the art.

It may be less expensive to fabricate each well of gas permeable multiple well plate 16 out of gas permeable material, including the well bottom, thereby eliminating the seal joint. Then, if adherent culture is desired, a suitable scaffold can be placed at the bottom of the well. Care should be taken to ensure optical clarity if microscopic evaluation is desired. Any cell attachment surface known to those skilled in the art of cell culture can be placed in the wells. If the cell attachment surface is buoyant, making it a press fit into the well can keep it in the desired position. Many other methods of retaining it in position are also possible.

Figure 10A:
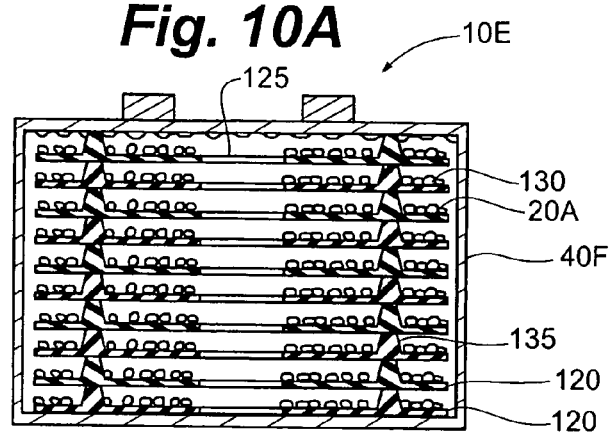
FIG. 10A and FIG. 10B show an embodiment of a gas permeable cell culture device configured with scaffolds for culturing adherent cells without need of a gas/liquid interface. It is linearly scalable in the horizontal and vertical direction creating superior efficiency relative to traditional adherent culture devices. It is capable of culturing cells on either one or both sides of the scaffolds. It can be operated in either the rolled or in the unrolled state.
Figure 10B:
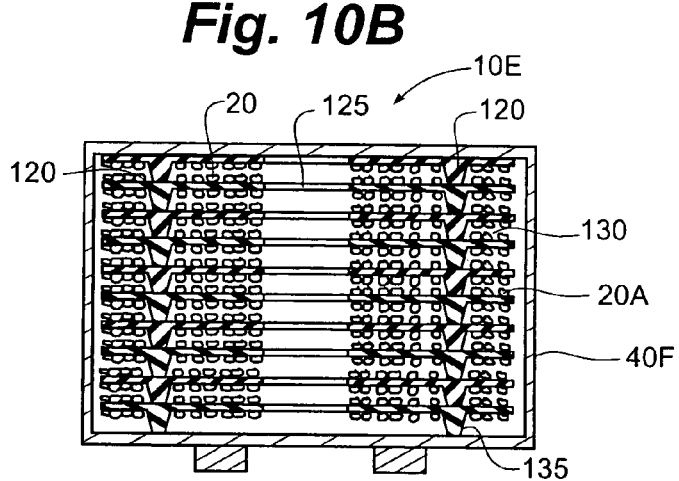

FIG. 10A and FIG. 10B show cross-sectional views of one embodiment of a gas permeable cell culture device that utilizes space more efficiently when culturing adherent cells. Scaffolds 120 reside within gas permeable cell culture device 10E. Sidewalls 40F are comprised of a gas permeable material, thereby allowing gas exchange through the sides of the device. In this manner, gas permeable cell culture device 10E is not limited in height, as scaffolds 120 can be scaled uniformly as height increases. Allowing more cells to be cultured is simply a matter of making the device taller, adding more scaffolds 120. In the preferred embodiment, the distance between each scaffold 120 is kept constant during scale up. For example, by configuring scaffolds 120 to have spacers 135, they can be kept an equal distance apart and retained parallel to the bottom of gas permeable cell culture device 10E, making scale up in the vertical direction linear. Pipette access opening 125 allows pipette access throughout gas permeable cell culture device 10E and provides an opening to vent gas as medium is added. Although shown in the center, pipette access can be in any location, or can be eliminated entirely in favor of any other form of liquid handling such as needles and septum. In FIG. 10A, cells 20A are well suspended in inoculum 130 and will distribute evenly about the upper surface of each scaffold 120, since the volume of inoculum 130 above each scaffold 120 is equal. If both sides of scaffold 120 are intended to culture adherent cells, inoculation can occur in two steps by inoculating one side of scaffolds 120 first, as shown in FIG. 10A. After cells have gravitationally deposited and attached onto the surface of scaffolds 120, gas permeable cell culture device 10E is then re-inoculated, rotated one hundred eighty degrees to expose the opposite side of scaffolds 120, and cells 20A are allowed to settle and attach to the exposed surface of scaffolds 120 as shown in FIG. 10B.

Post cell attachment, typically less than 24 hours to seed one side of the scaffolds, the device can be operating in any static position that is convenient, such as vertical, inverted, or on its side. If desired, it can be rolled if a user desires a format more similar to a roller bottle. Unlike traditional devices, the device can be filled completely with medium, as gas exchange occurs by way of the gas permeable walls and the need for a gas/liquid interface is not present. In this manner, the device is more efficient in its use of space than traditional devices since gas does not need to be present in the device for gas exchange of the culture. The limiting factors to the number of cells that can be cultured in the device include the amount of scaffold surface area, the volume of medium present, the gas permeability and thickness of the material used for the device walls, the distance the cells reside from the gas permeable walls of the device, and the type of cells being cultured.

Understanding the importance of the medium volume to scaffold area ratio when designing the gas permeable cell culture device can help predict the output of the device. For instance, if the culture has been historically conducted in a roller bottle, the medium volume to surface area of the roller bottle culture can be replicated in the gas permeable cell culture device. For example, if the existing culture had been performed in a traditional 850 $cm^2$ roller bottle using 150 ml of medium, and the gas permeable cell culture device was to have the same outside shape as the traditional bottle, the medium volume to surface area ratio could be held constant. A gas permeable cell culture device constructed in the shape of the traditional 850 $cm^2$ roller bottle can hold about 2200 ml of medium. That is a 14.67 fold increase in medium volume relative to the 150 ml medium volume of the traditional roller bottle. Therefore, a 14.67 fold increase in surface area, which is 12,470 $cm^2$, is needed to keep an equivalent medium to surface area ratio. Thus, when a gas permeable cell culture device contains 2200 ml of medium and has a scaffold surface area of 12,470 $cm^2$, it can be expected to culture the same number of cells as about fifteen traditional 850 $cm^2$ roller bottles that normally operate with 150 ml per bottle, and the feeding frequency should be about the same.

Figure 11:
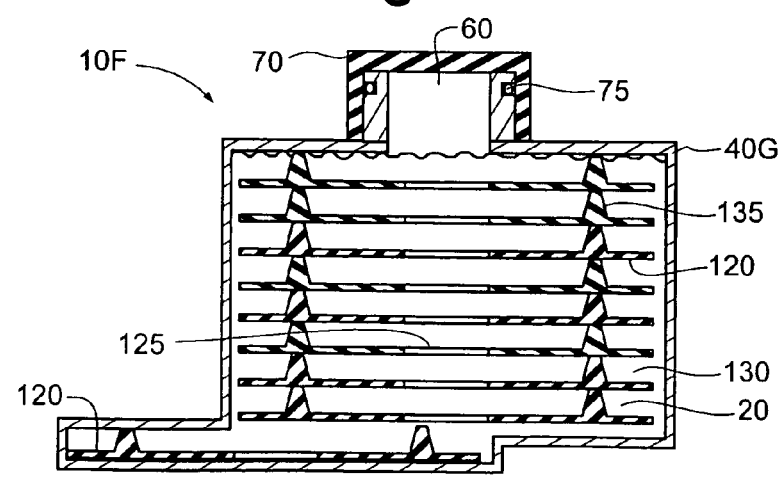
FIG. 11 is an embodiment of a gas permeable cell culture device configured with scaffolds, at least one of which is suitable for optimal microscopic cell assessment.

The ability to microscopically assess cell confluence is useful for many applications. If the lowest scaffold comprises the bottom of gas permeable cell culture device, it can be used to assess cell confluence. When the volume of medium residing above each scaffold is equal during inoculation, the amount of cells residing upon any of the scaffolds will be relatively equal throughout the culture. Thus, one scaffold can be representative of the others. For some microscopes, the ability to physically move the lowest scaffold into a position that allows microscopic observation by inverted scopes can allow a better assessment of confluence and morphology. The configuration shown in the cross-sectional view of FIG. 11 shows how this can be achieved. If wall 4GH is flexible, as will be the case when it is fabricated out of many gas permeable materials such as silicone, it can be pleated to allow movement of the lowest scaffold 120 relative to gas permeable cell culture device 10F. Microscopic evaluation can also be made possible by manufacturing gas permeable cell culture device 10F in the fixed position shown in FIG. 11, thereby eliminating the need to move the lowest scaffold 120 relative to gas permeable cell culture device 10F.

Figure 12A:
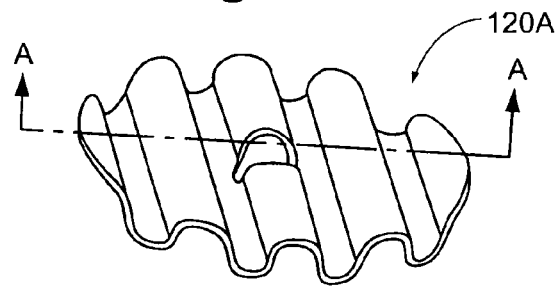
FIG. 12A, FIG. 12B, FIG. 12C, and FIG. 12D show embodiments of scaffolds configured to provide a further increase in surface area, bringing even more efficiency to the gas permeable cell culture device.
Figure 12B:
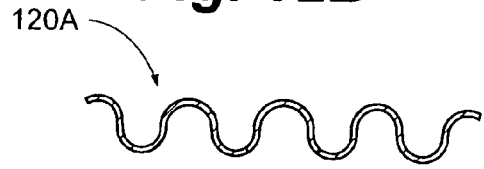
Figure 12C:
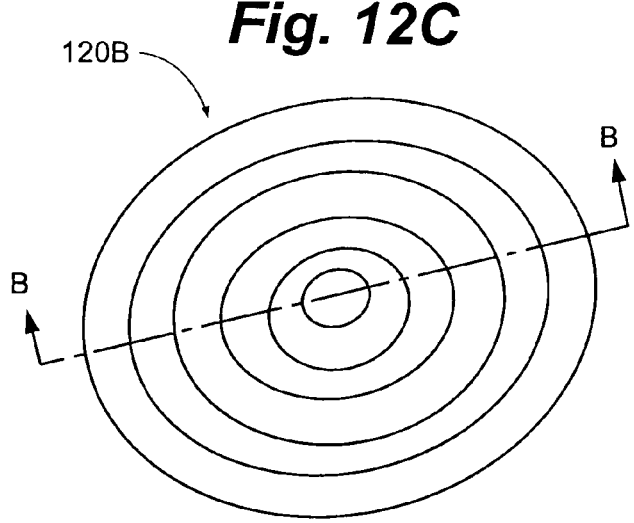
Figure 12D:
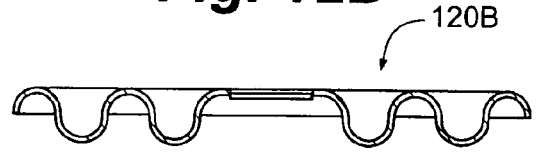

Although the scaffolds shown in FIG. 10A, FIG. 10B, and FIG. 11 are flat, they can be any geometric shape that allows cells to attach. For example, corrugating the surface can increase surface area relative to a planar surface, thereby increasing the amount of adherent cells that can reside upon a given scaffold. FIG. 12A shows a perspective view of a round corrugated scaffold 120A, which is corrugated in a linear direction. FIG. 12B shows cross-sectional view A-A. FIG. 12C shows a perspective view of round corrugated scaffold 120B, which is corrugated in the circular direction, and FIG. 12D shows cross-sectional view B-B. For some applications in which a high rate of gas transfer is needed to support highly active cells, the configuration of FIG. 12A may be superior because the channels for gas transfer are unobstructed by the edge of the scaffold, as is the case for the configuration of FIG. 12C. For other applications in which the gas permeable cell culture device is rolled, the configuration of FIG. 12C may be superior because the shape will minimize turbulence, which could cause cell shear.

The configurations, methods of microscopically viewing, and methods of increasing scaffold area such as those described in FIG. 10A, FIG. 11, and FIG. 12, can be integrated into a multiple well format. These configurations are completely scalable in size. FIG. 9B shows high surface area well 46, configured with multiple scaffolds 120 maintained a predetermined distance apart by spacers 135. Making them the size of the wells of a typical traditional multiple well tissue culture plate will allow a substantial increase in the number of adherent cells present per well. The walls 41A are preferably gas permeable.

Figure 13:
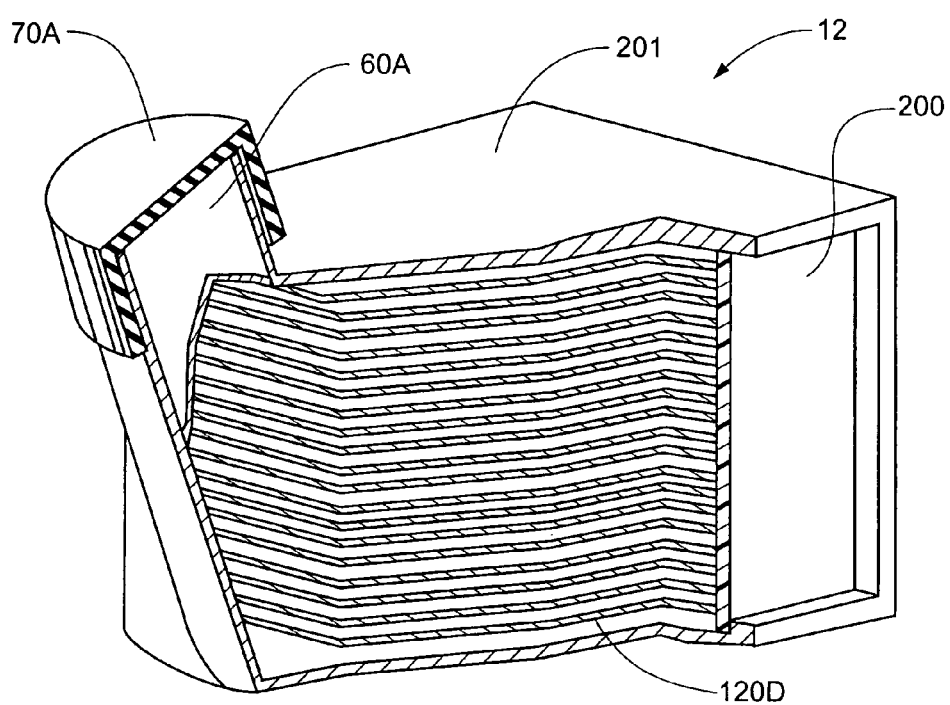
FIG. 13 is an embodiment of a gas permeable cell culture device with scaffolds and at least one sidewall comprised of gas permeable material. The need for a gas/liquid interface as a means of gas exchange is eliminated, leading to more efficient use space and the related cost benefits in terms of sterilization, shipping, storage, use of incubator space, and disposal.

FIG. 13 shows a cutaway view of configuration for a gas permeable cell culture device that is useful for culturing cells in a format similar to that of a tissue culture flask. In this embodiment, at least one wall of the device provides gas transfer. This device is beneficial because it allows the gas permeable cell culture device to retain the same attributes as the traditional tissue culture flask while achieving a more compact use of space. The desirable attributes include easy medium delivery and removal by way of pouring or pipetting, microscopic observation capability, the ability to easily see color changes in the medium that may indicate contamination or pH changes, and capability for device stacking to make the most efficient use of shipping, storage, and incubator space. However, it is superior to the tissue culture flask because the gas/liquid interface required for tissue culture flask operation is eliminated and one or more scaffolds can be present. In the embodiment shown, gas permeable cell culture device 12 is comprised of a liquid tight enclosure with at least one gas permeable wall 200. Medium access port 60A is covered by cap 70A. Scaffolds 120D are oriented parallel to each other, with a gap between them to allow inoculum and medium to reside in between each scaffold 120D. Preferably, scaffolds 120D are positioned an equal distance apart to allow an equivalent volume of inoculum or medium to reside above each of them. The gas permeable material of gas permeable wall 200 has the same attributes as those described for lower gas permeable material 30 of the embodiment shown in FIG. 4A. In the preferred embodiment, scaffolds 120D have identical material characteristics as those present in traditional tissue culture flasks. Top wall 201 and bottommost scaffold 120D are clear, allowing visual assessment of medium color as well as microscopic evaluation of the bottom scaffold 120D. Making the rear or other walls gas permeable can create more gas transfer capacity. That will have the effect of making it possible to further increase the footprint of gas permeable cell culture device 12. For example, if the gas transfer capacity of gas permeable wall 200 supports cells residing upon scaffolds 120D of a five inch width, making the opposing side wall gas permeable will allow enough gas transfer capacity when scaffolds 120D that are ten inches wide. Gas permeable cell culture device 12 is unlimited in scale up capacity in the vertical direction.

Figure 14B:
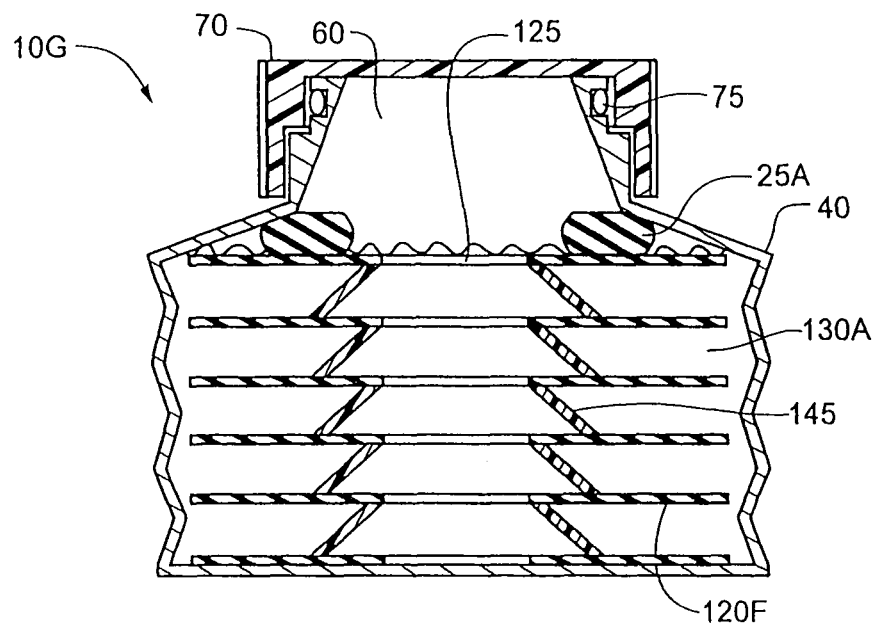
FIG. 14A, FIG. 14B, FIG. 14C, and FIG. 14D show views of an embodiment of a gas permeable cell culture device configured with scaffolds, the location of which can be adjusted for benefits that can include minimizing the use of trypsin, altering the ratio of medium to culture area, and minimizing shipping, inventory, and disposal space.
Figure 14A:
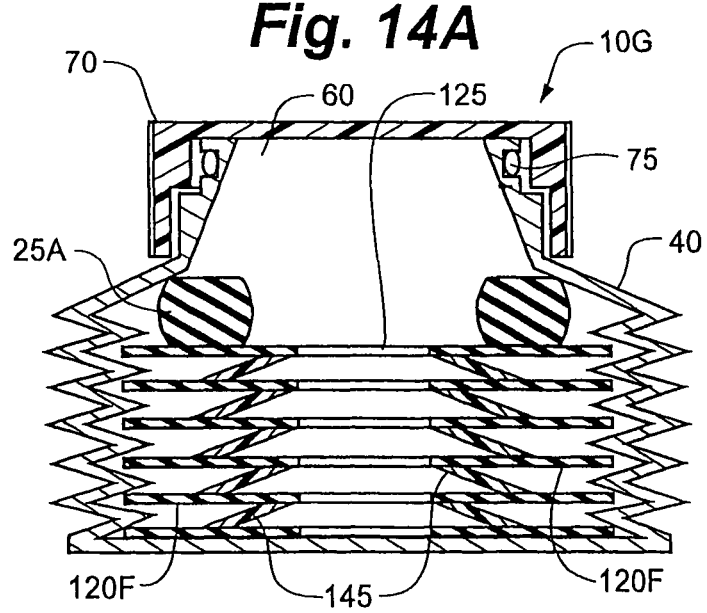
Figure 14C:
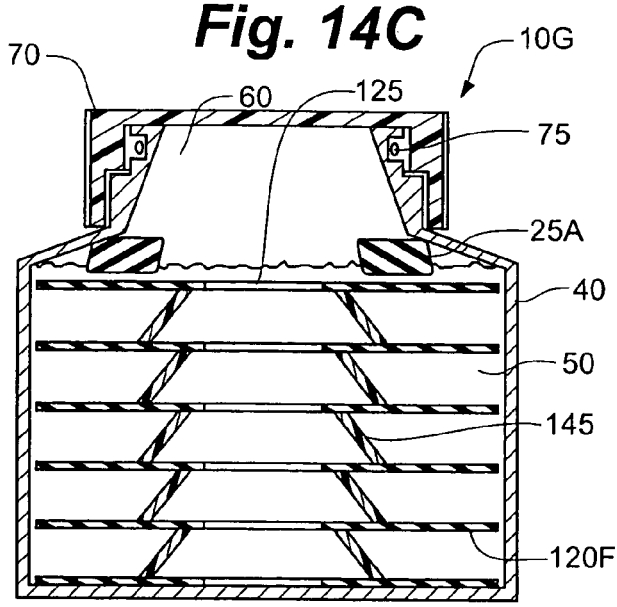
Figure 14D:
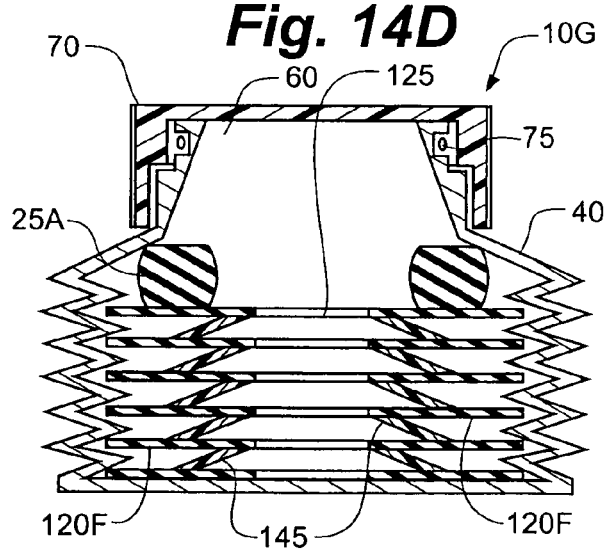

FIG. 14A through FIG. 14E show another method of utilizing space more efficiently when culturing cells. In this configuration, scaffolds 120F reside within gas permeable cell culture device 10G, which is capable of expanding in volume as medium 50 is added. In FIG. 14A, gas permeable cell culture device 10G is in a collapsed position under its own weight. That allows efficient use of space for shipping, sterilization, and storage prior to use. Scaffolds 120F are as close to each other as possible. Each scaffold 120F is molded with spring arms 145 that exert force on the lower, neighboring scaffold 120F. Spring arms 145, in compression, want to distend, but cannot because the weight of the upper portion of gas permeable cell culture device 10G exceeds the spring force. In FIG. 14B, gas permeable cell culture device 10G has risen in height in response to the force exerted by the addition of inoculum 130A against buoyant shoulder 25A. The displacement of inoculum 130A by buoyant shoulder 25A exerts an upward force that, when combined with the spring force of spring arms 145K, exceeds the weight of the upper portion of gas permeable cell culture device 10G. Scaffolds 120F separate and maintain an equal distance from each other due to the force exerted by spring arms 145 against their lower, neighboring scaffold 120F. Maintaining an equal distance from each other is particularly beneficial during inoculation, when the volume of inoculum 130A residing directly above each of scaffolds 120F dictates the amount of cells that will be deposited onto each of scaffolds 120F. By allowing an equal volume of inoculum 130A to reside above each scaffold 120F, and equal number of cells can reside upon each scaffold 120F. In FIG. 14C, gas permeable cell culture device 10G has risen in height again relative to FIG. 14B in response to the addition of medium 50 as the cell population expands and nutrient demand increases. Scaffolds 120F further separate and maintain an equal distance from each other due to the force exerted by spring arms 145 against their lower, neighboring scaffold 120F. The constant distance between each of scaffolds 120F ensures a constant medium 50 volume to surface area ratio at all cell locations, reducing the potential for gradient formation. In FIG. 14D, gas permeable cell culture device 10G has collapsed due to the removal of medium 50 and loss of upward force of buoyant shoulder 25A. It is now at an efficient size for disposal. In the event that adherent cell recovery is needed, allowing gas permeable cell culture device 10G to collapse is beneficial when removing medium 50 and adding trypsin. In this manner, only a small volume of trypsin is needed to recover cells. Those skilled in the art will recognize that many other methods of altering the height of gas permeable cell culture device 10G can be applied.

Figure 14E:
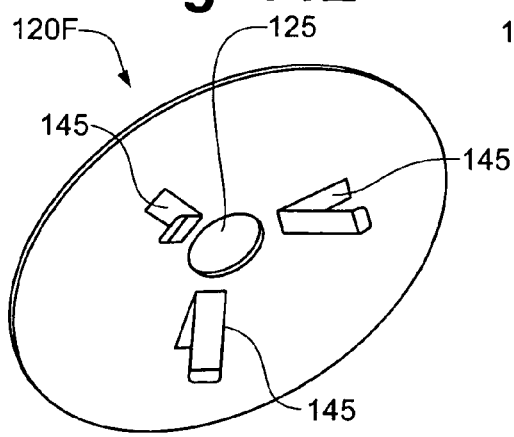
FIG. 14E shows a scaffold configured to maintain equal distance between it, and its neighboring scaffolds.

Spring arms 145 can be molded directly into scaffold 120F, as shown in the perspective view of FIG. 14E. A spring arm 145, preferably located in at least three places, ensures that scaffold 120F remains in plane and parallel to its neighboring scaffold 120F. Although any material conducive to cell attachment is acceptable, a preferred material for scaffold 120F is polystyrene, which is quite brittle. Therefore, care should be taken to ensure that spring arms 145 are configured in accordance with good molded part design to prevent cracking under stress. Techniques for low stress part design are well known to those skilled in the art of plastic part design.

Figure 15A:
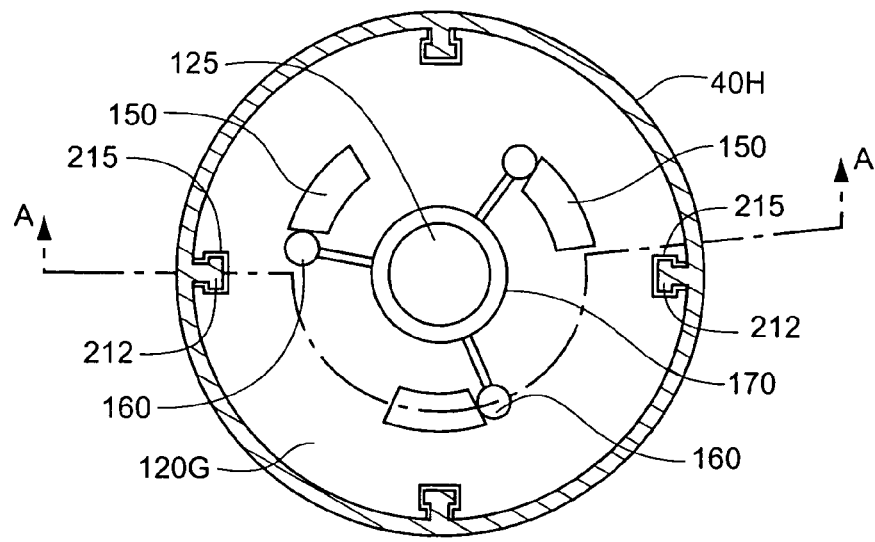
FIG. 15A, FIG. 15B, and FIG. 15C show an embodiment of scaffolds configured such that the distance between each can be altered while the body of the device remains at a fixed height. This embodiment can provide benefits that include minimizing the use of trypsin, or altering the ratio of medium to culture area, without need to make the body of the device change shape.
Figure 15B:
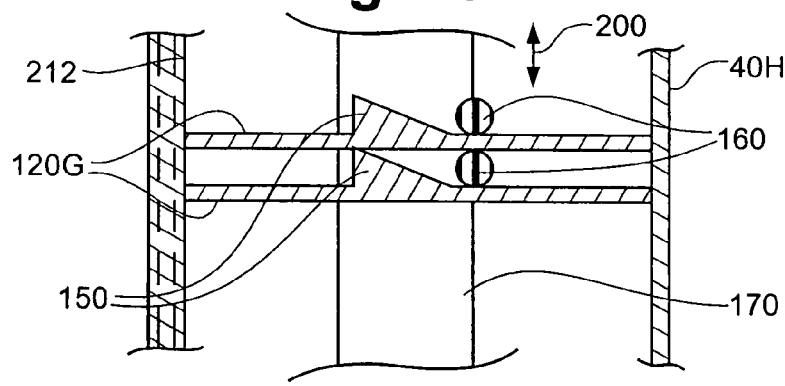
Figure 15C:
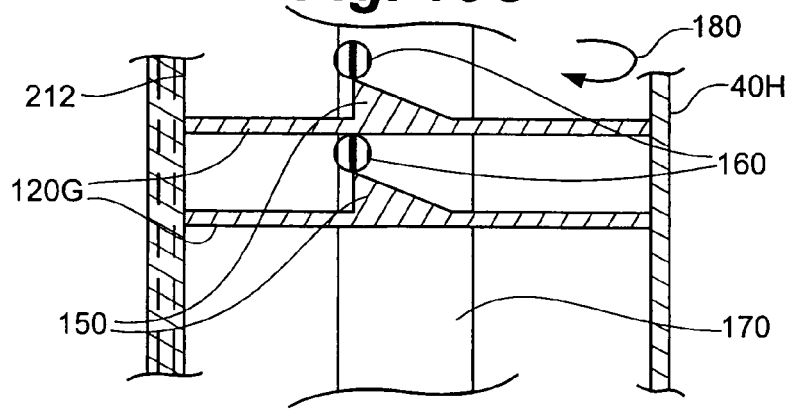

Moving the position of the scaffolds independent of the height of the gas permeable cell culture device may be desired. For example, this may be practical when it is more economical to configure the gas permeable cell culture device with non-extending walls, but the application can still benefit by altering the medium volume to surface area ratio above each of the scaffolds during culture. FIG. 15A through FIG. 15C show one embodiment for achieving that objective. For clarity, only a portion of the gas permeable cell culture device is shown. In the top view of a portion of a gas permeable cell culture device shown in FIG. 15A, three elevation posts 160 are positioned to travel up each of three ramps 150 in order to change the distance between the scaffolds.

The method of varying the distance between scaffolds can best be understood by reviewing FIG. 15B and FIG. 15C.

FIG. 15B shows cross-section A-A of FIG. 15A. As shown in FIG. 15B, two scaffolds 120G are shown the position in which the distance between them is at a minimum. Ramp 150 emanates from the top of scaffold 120G and elevation post 160 emanates from scaffold locator screw 170. Elevation post 160 has not begun travel up ramp 150. It can be seen that the minimum distance between scaffolds is dictated by the height of ramp 150, which makes contact with the underside of the scaffold 120G that resides above it. Referring to FIG. 15C, scaffolds 120G are in the position of maximum distance between them. Scaffold locator screw 170 has been rotated in the direction of rotation arrow 180, causing elevation post 160 to rise up ramp 150 and elevate the scaffold 120G residing above it. When elevation post 160 resides at the highest point of ramp 150L, the maximum distance between scaffolds 120L is attained as is equal to the height of ramp 150 plus the height of elevation post 160. Scaffolds 120G should be prevented from rotating when scaffold locator screw 170 is turned, thereby allowing ramp 150 to remain in a fixed position while elevation post 160 travels up it. This can be achieved by mating scaffolds 120G to the interior of the gas permeable cell culture device wall by way of a tongue and groove arrangement. As best shown in the top view of a scaffold of FIG. 15A, tongue 212 emanates from gas permeable wall 40H and mates to groove 215 in each scaffold 120G. Not only does this prevent rotation of scaffold 120G during rotation of locator screw 170, it also prevents gas permeable wall 40H from pulling away from scaffold 120G. In this manner, the shape of the gas permeable cell culture device is retained. Locator screw 170 can be configured to allow a sterile pipette tip to rotate it, thereby preventing contamination of the device and allowing the use of standard laboratory tools to rearrange the distance between scaffolds.

The invention will be further described with reference to the following non-limiting Examples.

EXAMPLES

Example 1

The Effect of Medium Height upon Cell Growth and Antibody Production

Evaluations were conducted in order to assess the impact of altering medium height upon cell growth and antibody production in a device comprised of a lower gas permeable material. The effect of altering the gas permeable material surface area to medium volume ratio was also assessed. Single compartment test fixtures configured with a lower gas permeable materials and the capacity to hold medium at heights beyond conventional wisdom were compared to single compartment control test fixtures that held medium at a height within the bounds of conventional wisdom. Comparisons were made relative to the 1.6 cm medium height limits specified for the Si-Culture bag (U.S. Pat. No. 5,686,304). Control test fixtures were configured to house medium at a height of 1.6 cm, and the gas permeable material used for of all test fixtures consisted of gas permeable material obtained from actual Si-Culture™ bags.

Figure 16:
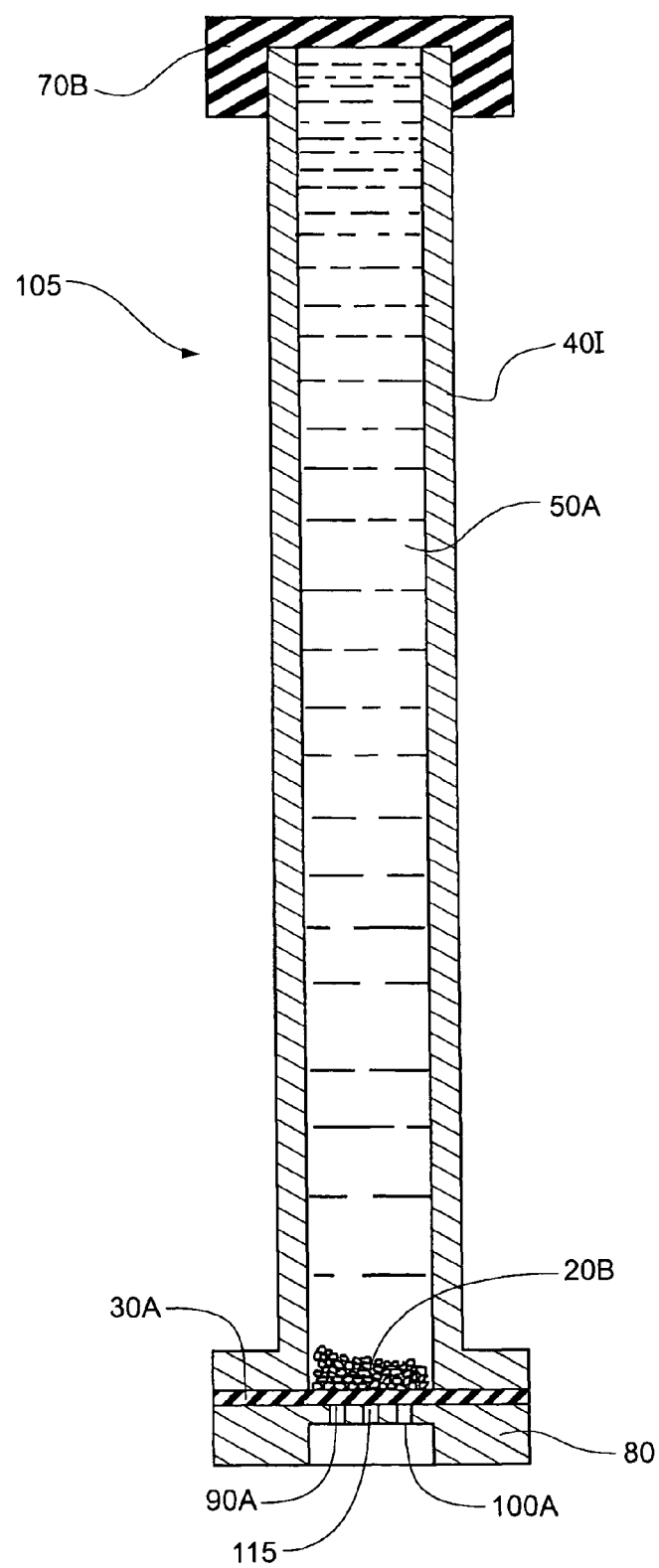
FIG. 16 is a cross-sectional view of a tubular test fixture used to assess the effect of medium height on cell growth and antibody production. Biological evaluations using this test fixture demonstrated the benefit of increasing medium height beyond the limits of conventional wisdom, and the ability to reduce the gas permeable surface area to medium volume ratio of prior devices. These surprising results allow device configurations not previously contemplated to exist.

Tubular test fixtures 105 were constructed as shown in FIG. 16. Walls 40I were machined out of Ultem 1000 (high temperature polycarbonate) cylindrical stock, resulting in a tube with an inner diameter of 1.00 inch and an outer diameter of 1.50 inch. The thick walls ensured that gas transfer through the walls would not assist the cultures. Lower gas permeable material 30A was fabricated from 0.0045 inches thick sheets of silicone removed from Si-Culture198 bags and secured in a liquid tight manner to the bottom of the machined tube yielding a 5.07 cm² growth area for cells 20B to reside upon. Lower gas permeable material support 80M was also machined out of Ultem 1000. Lower gas permeable material 30A was held in the horizontal position by mesh 115 which maintained gas compartment 90A. Mesh 115 was comprised of 0.020 inch diameter strands at 16 strands per inch. Lower gas access openings 100A allowed gaseous communication with the 5% $CO_2$, 95% R.H., and 37 C ambient environment. Comparisons were made for the capacity of the devices to grow cells 20B when differing amounts of medium 50A resided within the test fixture. Cap 70B, secured tightly to walls 40I, protected tubular test fixture 105 from contamination. Tests compared the results when medium 50A resided at a height of about 1.6 cm, 3.2 cm, 5.6 cm, 10.2 cm, 15.3 cm, and 20.4 cm above the cells. Medium 50A consisted of Hyclone HyQSFM4MAb-Utility supplemented with 10% Hyclone FBS. Cells 20B were murine hybridoma cells secreting IgG, inoculated at a seeding density of $0.76 \times 10^6$ per cm² of lower gas permeable material 30A. Ambient conditions were 5% $CO_2$, 95% R.H., and 37 C. Periodic cell counts and monoclonal antibody production measurements by ELISA were taken. TABLE 1 shows the results.

The data of TABLE 2 clearly shows the advantages of altering the geometry of gas permeable cell culture devices to allow more medium to reside above the cells. For example, the last row shows that when the device is allowed to hold medium at a height that is 12.75 times greater than the traditional cell culture bag, it is capable of culturing 2.91 fold more cells per cm² of floor space occupied, producing 11.99 times more monoclonal antibody (Mab) with only a 2.83 fold increase in the time to complete production. Also, when the gas permeable material surface area to medium volume ratio is compared to that of the Si-Culture™ bag, dramatically reduced ratios are possible. Cultures were effectively grown even when the ratio was only 4% of that used by the Si-Culture™ bag. That allows a wider variety of device configurations to exist, including allowing the device footprint to remain fixed as medium height is increased. It also minimizes the effects of evaporation, as more medium is present per cm² of gas permeable surface area.

Importantly, this data demonstrates that device footprint can remain small as the culture is increased. TABLE 3 shows the surface area of the device footprint needed to house the volume of medium residing in the test fixtures. The first row shows the medium volume in the test fixture. The second row shows the footprint area of the test fixture, which remained fixed as more and more medium was added. The third row

TABLE 1

Medium Height Affect Upon Cell Growth and Antibody Production

| Volume of medium (ml) | Height of medium above gas permeable material (cm) | Gas permeable surface area to medium volume ratio (cm²/ml) | Maximum live cells per device ($\times 10^6$) | Maximum live cells per cm² gas of permeable material ($\times 10^6$) | Mab produced per test fixture (ug) | Time to maximum amount of mab produced (days) | Mab per ml of medium consumed (ug/ml) |
|---|---|---|---|---|---|---|---|
| 8.1 | 1.60 | 0.63 | 29.7 | 5.85 | 2742 | 9 | 339 |
| 16.2 | 3.20 | 0.31 | 51.0 | 10.05 | 7395 | 12 | 457 |
| 25.8 | 5.09 | 0.20 | 59.1 | 11.65 | 10673 | 18 | 374 |
| 51.7 | 10.20 | 0.10 | 61.1 | 12.05 | 15252 | 15 | 295 |
| 77.6 | 15.31 | 0.07 | 67.2 | 13.25 | 23044 | 22 | 299 |
| 103.4 | 20.39 | 0.05 | 86.4 | 17.04 | 32881 | 25 | 318 |

Dividing each parameter measured in any given test fixture by the corresponding parameter of the test fixture representing conventional wisdom (i.e. 1.6 cm) clearly shows the advantages of allowing medium to reside at heights beyond conventional wisdom. Gas permeable surface area to medium volume ratio is determined by dividing the ratio of the test fixture by the ratio of the Si-Culture™ bag when it contains medium at a height of 1.6 cm (i.e. 1.25 cm²/ml). TABLE 2 presents the data of TABLE 1 in this manner.

shows the footprint surface area that would be required in a typical bag to hold the volume of medium residing in the test fixture. In this case, the footprint is shown for a Si-Culture™ bag when it contains the volume of row one at the manufacturers recommended medium height of 1.6 cm. The fourth row shows the difference in footprint area. For example, when the test fixture contains 103.4 ml of medium, the Si-Culture™ bag when operated according to manufacturers recommendation would have a footprint of 64.6 cm², but the test fixture

TABLE 2

Normalized data

| Normalized by height of medium above gas permeable membrane | Normalized by maximum live cells per device | Normalized by gas permeable surface area to medium volume ratio relative to Si-Culture™ bag | Normalized by Mab produced per test fixture | Normalized by Mab per ml of medium consumed | Normalized by time to attain maximum Mab amount | Normalized by footprint of space occupied |
|---|---|---|---|---|---|---|
| 1.00 | 1.00 | 50% | 1.00 | 1.00 | 1.00 | 1.00 |
| 2.00 | 1.72 | 25% | 2.70 | 1.35 | 1.50 | 0.50 |
| 3.18 | 1.99 | 16% | 3.89 | 1.11 | 2.00 | 0.28 |
| 6.38 | 2.06 | 8% | 5.56 | 0.87 | 1.67 | 0.16 |
| 9.57 | 2.26 | 6% | 8.40 | 0.88 | 2.50 | 0.10 |
| 12.75 | 2.91 | 4% | 11.99 | 0.94 | 2.83 | 0.08 | only has a footprint of 5.1 cm$^2$. Thus, the test fixture that allowed medium to reside at a height of 20.39 cm only needed a footprint of 8% of that needed for a Si-Culture™ bag to produce roughly the same amount of Mab.

TABLE 3

Much more efficient use of floor space.

| | | | | | | |
|---|---|---|---|---|---|---|
| Volume of medium in device (ml) | 8.1 | 16.2 | 25.8 | 51.7 | 77.6 | 103.4 |
| Test fixture footprint (cm$^2$) | 5.1 | 5.1 | 5.1 | 5.1 | 5.1 | 5.1 |
| Bag footprint with medium at 1.6 cm high (cm$^2$) | 5.1 | 10.1 | 16.1 | 32.3 | 48.5 | 64.6 |
| Ratio of test fixture footprint to bag footprint (%) | 100% | 50% | 32% | 16% | 11% | 8% |

Benefits relative to all of the conventional configurations are numerous. The unwieldy shape of traditional cell culture bags can be avoided allowing a wide variety of benefits to accrue related to more efficient use of incubator space, easier medium delivery and removal, and reduced contamination risk. The small volume of medium present in gas permeable cartridges can be increased substantially by making them taller, and reducing the ratio of gas permeable membrane to medium volume capacity. That has the effect of allowing fewer units to be needed during scale up. For traditional gas permeable formats of the petri dish and multiple well plate, more cells can reside per unit without increasing the footprint of the devices, or the number of devices needed, and the frequency of feeding can be reduced. Minimized evaporative effects can be achieved in all configurations because the gas permeable surface area to medium volume ratio can be significantly reduced.

Example 2

Effect of Thickness of Gas Permeable Silicone on Cell Growth

Conventional wisdom, as dictated by U.S. Pat. No. 5,686,304 and U.S. patent application Ser. No. 10/183,132, and the design of commercially available gas permeable products that use silicone, dictates that silicone thickness of greater than 0.005 inches should not be used. However, increasing the thickness is advantageous from a manufacturing and product reliability standpoint. Therefore, evaluations were conducted to assess the impact of the thickness of a lower silicone gas permeable material on cell growth. The material thickness of conventional wisdom was compared to the same material at increasing thickness.

Tubular test fixtures were constructed as shown in FIG. 16. Walls were machined out of Ultem 1000 (high temperature polycarbonate) cylindrical stock, resulting in a tube with an inner diameter of 1.00 inch and an outer diameter of 1.50 inch. Four distinct thickness configurations of lower gas permeable material were created from sheets of silicone removed from Si-Culture™ bags. Lower gas permeable material 30A was made into double, triple, and quadruple layers, formed by adhering the silicone sheets together using UV curing silicone glue distributed evenly about the face and sheets were laminated together leaving no air gaps between them. Post curing, the laminated sheets and a single sheet control were secured in a liquid tight manner to the bottom of the machined tube yielding a 5.07 cm$^2$ growth area for cells to reside upon. Tests were conducted in triplicate. Lower gas permeable material 30A was held in the horizontal position by lower gas permeable material support 80, configured as described in Example 1. Tests compared the results when medium resided at heights of 20.4 cm above the cells. Medium consisted of Hyclone HyQSFM4MAb-Utility supplemented with 10% Hyclone FBS. Murine hybridoma cells were inoculated at a seeding density of 4.3×10$^6$ live cells per square cm of lower gas permeable material. Ambient conditions were 5% CO2, 95% R.H., and 37 C. Periodic cell counts and glucose measurements were taken. TABLE 4 shows the results.

TABLE 4

Effect of Thickness of Gas Permeable Silicone on Cell Growth

| Membrane Thickness(in) | Maximum viable cells per cm$^2$(×10$^6$) | Normalized: Membrane Thickness | Normalized: Maximum viable cells per cm$^2$ |
|---|---|---|---|
| 0.0045 | 15.2 | 1.00 | 1.00 |
| 0.016 | 15.5 | 3.56 | 1.02 |
| 0.024 | 13.49 | 5.33 | 0.89 |
| 0.033 | 12.0 | 7.33 | 0.79 |

The data was normalized by referencing it against the data collected for the single 0.0045 inch thick sheet that represents conventional wisdom. It can clearly be seen that the effect of dramatically increasing thickness does not have a significantly negative impact on the capacity to support cell growth. When the material thickness was increased about four-fold, from 0.0045 inch to 0.016 inch, there was no affect upon cell growth. When the silicone membrane thickness was increased 5.33 fold, from 0.0045 inch to 0.024 inch, the growth capacity was diminished by only 11%. Likewise, a 7.33 fold increase in thickness beyond conventional wisdom resulted in growth capacity being diminished by only 21%. In many cell culture applications, such as hybridoma culture for monoclonal antibody production, 79% viability is routinely accepted. For example, in the CELLine™ products, hybridoma viability is commonly at 50%, as described in the operating instructions. Thus, device design can accommodate thicker silicone walls without a dramatic reduction in performance. Fabrication and functional improvements may result from increasing the thickness, such as simplified liquid injection molding or less pinhole potential. In summary, it is possible to design a highly functional cell culture device with thicker walls than previously believed possible.

Example 3

The Ability to Culture Cells at a High Liquid Height in a Rolled and Unrolled Device Evaluations were conducted to assess the advantages that could be obtained by configuring gas permeable cell culture devices in ways that differ from conventional wisdom. Two general formats were evaluated, 1) unrolled gas permeable devices and 2) rolled gas permeable devices. In the unrolled gas permeable device configuration, medium height was well beyond the limits imposed by conventional wisdom. The ratio of gas permeable surface area to medium volume was reduced far below that of conventional wisdom. In the rolled gas permeable device configuration, medium was allowed to reside farther away from the gas permeable wall, and more medium was allowed to reside per device, than that of the state of the art gas permeable rolled bottles.

The production of monoclonal antibody is a common application in cell culture bags and roller bottles. A traditional 850 cm$^2$ roller bottle functioned as a control. Test fixtures were constructed in accordance with the embodiments shown in FIG. 4, and dimensionally configured to have the same dimensions as a traditional 850 cm² Corning® roller bottle. The gas permeable material was the same as that of the Si-Culture™ bag, as further defined in U.S. Pat. No. 5,686,304. The gas permeable surface area of non-rolled test fixture was limited to that of the bottom surface of the fixture, and was 98 cm². The sidewalls were not gas permeable. The gas permeable surface area of the rolled test fixture was limited to that of the entire cylindrical sidewall surface of the fixture, and was 850 cm², and the ends were not gas permeable. Medium consisted of Hyclone SFM4MAb, supplemented with 2.5% Hyclone FBS. Each test fixture was inoculated with a cell density of $0.04 \times 10^6$ murine hybridoma cells per ml of medium used. The test fixtures each received 2050 ml of medium. Ambient conditions were 5% $CO_2$, 95% R.H., and 37 C.

The traditional roller bottle received 255 ml of medium, the maximum amount of medium recommended for use in roller bottles. The presence of antibody was determined by ELISA. TABLE 5 shows the results.

TABLE 5

Effect of rolling versus standing on antibody production time

| Test Fixture Style | Maximum amount of antibody produced (mg) | Time to reach maximum production (days) |
|---|---|---|
| Unrolled Novel Device | 289 | 16 |
| Rolled Novel Device | 302 | 13 |
| Traditional Roller Bottle | 33 | 13 |

TABLE 5 shows how the rolled and the non-rolled gas permeable test fixtures, which occupied the same amount of space as the traditional roller bottle control, were able to produce about nine times as much antibody. TABLE 5 also demonstrates how the rolled gas permeable format can be used to decrease the amount of time needed to generate antibody relative to its standing gas permeable counterpart. A 20% reduction in time, three days, was attained. Importantly, both the roller and unrolled formats can create a at least a nine fold improvement in efficient geometry in terms of space, leading to reduced cost of sterilization, shipping, storage, labor, incubator space, and disposal when compared to the traditional roller bottle.

The results also clearly demonstrate the advantage obtained by configuring gas permeable devices in ways that depart from conventional wisdom. The height of medium in the unrolled test fixture was about 20.9 cm, over ten times the highest recommended height of traditional cell culture bags. Had the device been structured with 2.0 cm of medium height, it would have needed a footprint of 1025 cm² to house an equivalent volume of medium, which is over ten times the footprint of the unrolled test fixture.

Benefits of geometry of the rolled gas permeable device were numerous. The rolled test fixture contained a volume of medium nearly eight times the maximum volume of medium recommended for traditional roller bottles (255 ml), over four times the medium volume of Rotary Cell Culture System™ from Synthecon Inc., nearly five times the medium volume of the MiniPERM, and well beyond that allowed in the patent proposals of Spaudling, Schwarz, Wolf et al., and Falkenberg et al. Also, medium resided up to 5.6 cm from any portion of the gas permeable wall of the test fixture, over double the limit specified in the patent proposals of Spaudling, Schwarz, and Wolf et al. The rolled test fixture was able to function on a standard roller rack, as opposed to the commercially available Rotary Cell Culture System™ from Synthecon™ Inc., and the MiniPERM™ from Vivascience Sartorius Group, which all require custom equipment to roll. Thus, the scale up efficiency of the rolled gas permeable device is much superior to other devices and approaches.

Example 4

Ability to Culture Adherent Cells in the Absence of a Gas/liquid Interface

Evaluations were conducted to assess the ability to culture adherent cells without the presence of a gas/liquid interface by allowing gas exchange to occur via gas permeable walls. A test fixture was constructed in a manner, as shown in FIG. 17, that eliminated the possibility of gas transfer by way of a gas/liquid interface. Gas permeable wall test fixture 12 consisted of a rectangular liquid tight enclosure 241, configured with one gas permeable wall 200A and five non-gas permeable walls 210. Gas permeable wall 200A was composed silicone membrane, approximately 0.0045 inches thick, purchased from Medtronic Inc. (Minneapolis). This membrane is used by Medtronic to fabricate the Si-Culture™ bag. Fluid delivery port 220 and fluid removal port 230 allow inoculation and feeding. Bottom attachment scaffold 240 consisted of a section of plastic removed from a Falcon tissue culture flask in order to provide an equivalent attachment surface as the control Falcon™ T-175 tissue culture flask. The inner dimensions of enclosure 241 were 6 cm deep, 10 cm wide, and 0.635 cm high. Thus, gas permeable wall 200A was 10 cm wide and 0.635 cm high creating a surface area of 6.35 cm². Bottom attachment scaffold 240 was 10 cm wide and 6 cm deep, allowing an attachment surface of 60 cm². Gas permeable wall test fixture 12 was filled entirely medium during inoculation, thereby eliminating any gas/liquid interface. Thus, gas exchange could only occur by way of diffusion in the direction perpendicular to gas permeable wall 200A. Inoculum consisted of 60,000 live BHK cells (98% viability) suspended in 38.1 ml of EMEM medium supplemented with 10% Hyclone FBS and 1% L-glutamine. Thus, the seeding density was 10,000 live cells per cm² of available attachment scaffold 240 area. The surface area of gas permeable membrane to volume of medium was 0.167 cm²/ml. The surface are of gas permeable membrane to surface area of attachment scaffold was 0.106 cm²/cm². The control T-175 tissue culture flask was inoculated with the same cells, at equivalent seeding density and viability. Gas permeable wall test fixture 12 and the T-175 control were placed in a standard cell culture incubator at 5% $CO_2$, 95% R.H., and 37° C.

Figure 20:
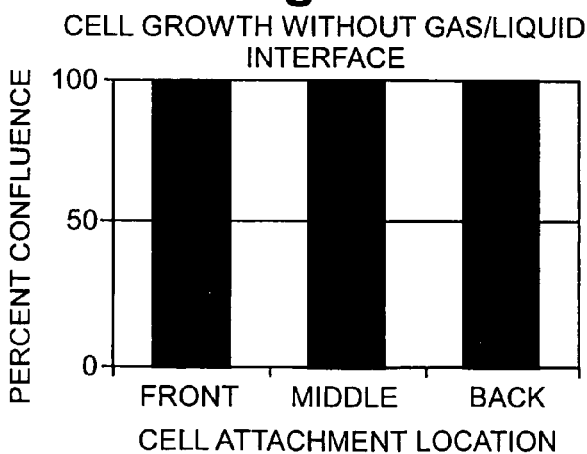
FIG. 20 is a cell distribution pattern, as described in Example 4.

Cells settled gravitationally onto bottom attachment scaffold 240 and the control T-175 flask, and the cultures were maintained until confluence was reached. Both the test fixture and the control exhibited a confluent monolayer over the entire attachment scaffold. By visual microscopic comparison, the cell density of both gas permeable test fixture 12 and the T-175 control flask appeared nearly identical. The T-175 flask was trypsinized, cells were counted, and it was determined that cells had reached a density of approximately 190,000 cells per cm². The test fixture was subjected to Wright Giemsa staining to determine the distribution of cells over bottom attachment scaffold 240. FIG. 20 shows the distribution pattern, where "Front" is in proximity of gas permeable wall 200, "Middle" is about midway between gas permeable wall 200 and opposing non-gas permeable wall 210, and "Back" is in proximity of opposing non-gas permeable wall 210.

FIG. 20 clearly indicates that cells will grow to confluence upon a scaffold in the absence of a gas/liquid interface, mechanical mixing, or perfusion, when a wall of the device is gas permeable. Thus, gas transfer by way of walls is adequate for cell culture devices of the types described herein including those shown in FIG. 9A, FIG. 9B, FIG. 10A, FIG. 10B, FIG. 11, and FIG. 14A through FIG. 14E to fully function. Example 4 also indicates that only one of the walls of a gas permeable cell culture device needs to be comprised of gas permeable material, thereby opening up a wide array of device design options. For example, a gas permeable device could be configured in a traditional T-Flask format by making a sidewall gas permeable. In this manner, more medium could be made available for the culture or the device profile could be reduced since no gas/liquid interface is needed.

Example 5

The Ability to Culture Cells on Multiple Attachment Scaffolds in the Absence of a Gas/liquid Interface Evaluations were conducted to assess the ability to culture adherent cells on multiple scaffolds without the presence of a gas/liquid interface. Gas exchange occurred via a gas permeable device wall. Gas permeable test fixtures were constructed in a manner, as shown in FIG. 18, that eliminated the possibility of gas transfer by way of a gas/liquid interface. Multiple scaffold test fixture 14 consisted of a rectangular liquid tight enclosure configured with one gas permeable wall 200B and five non-gas permeable walls 210A. Gas permeable wall 200B was composed of molded silicone material, 0.015 thick. Fluid delivery port 220A and fluid removal port 230A allow inoculation and feeding. Attachment scaffolds 240A consisted of plastic removed from NUNC™ Cell Factory cell culture devices. The inner dimensions of multiple scaffold test fixture 14 were 15.24 cm long, 7.62 cm wide, and 2.54 cm high. Thus, gas permeable wall 200B was 7.62 cm wide and 2.54 cm high creating a gas permeable material surface area of 19.35 cm$^2$. Each attachment scaffold 240A was 6.6 cm wide and 15.03 cm long, creating an attachment surface area of 99 cm$^2$ per attachment scaffold 240A.

In one test group of multiple scaffold test fixtures 14, four attachment scaffolds 240A were arranged vertically, one above the other, with a 5.08 mm gap between each of them, resulting in a total attachment surface area of 396 cm$^2$ per device. The volume of medium within this version of multiple scaffold test fixture 14 was 195 ml. The surface area of gas permeable membrane to volume of medium was 0.099 cm$^2$/ml. The surface area of gas permeable membrane to total surface area of attachment scaffolds 240A was 0.049 cm$^2$/cm$^2$.

In another test group of multiple scaffold test fixtures 14, five attachment scaffolds were arranged vertically, one above the other, with a 2.54 mm gap between each of them, resulting in a total attachment surface area of 495 cm$^2$ per device. The volume of medium within each multiple scaffold test fixture was 170 ml. The surface area of gas permeable membrane to volume of medium was 0.114 cm$^2$/ml. The surface area of gas permeable membrane to total surface area of attachment scaffolds 240A was 0.039 cm$^2$/cm$^2$.

Multiple scaffold gas permeable test fixtures 14 were filled entirely with medium during inoculation, thereby eliminating any gas/liquid interface. Thus, gas exchange could only occur by way of diffusion in the direction perpendicular to the gas permeable wall. The seeding density was 15,000 live BHK cells per cm$^2$ of available attachment scaffold area. Medium consisted of Gibco GMEM supplemented with 10% Hyclone FBS and 1% Gibco Penicillin Streptomycin. The control T-175 tissue culture flask was also inoculated with BHK cells, at equivalent seeding density and viability, in 30 ml of the same medium composition. Multiple scaffold gas permeable test fixtures 14 and the T-175 control were placed in a standard cell culture incubator at 5% $CO_2$, 95% R.H., and 37° C.

Cells settled gravitationally onto each attachment scaffold 240A and the control T-175 flask, and the cultures were maintained until confluence was reached. Within four days, cultures were terminated. All attachment scaffolds 240A were removed from multiple scaffold gas permeable test fixture 14. By visual microscopic comparison, the cell density of both test groups of multiple scaffold gas permeable test fixtures 14 and the T-175 control flask appeared nearly identical, at approximately 95% confluence.

This demonstrates the ability to make much more efficient use of space by eliminating the need to maintain a gas headspace in a culture device. Since the device only holds the medium needed to support the culture, it can be significantly reduced in profile. The novel device is much more compact than the traditional T-flask, NUNC™ Cell Factory, and Corning CellStack™. This results in savings in sterilization, shipping, storage, and disposal cost. Furthermore, incubator space and flow hood space are used more efficiently.

Example 6

Figure 19A:
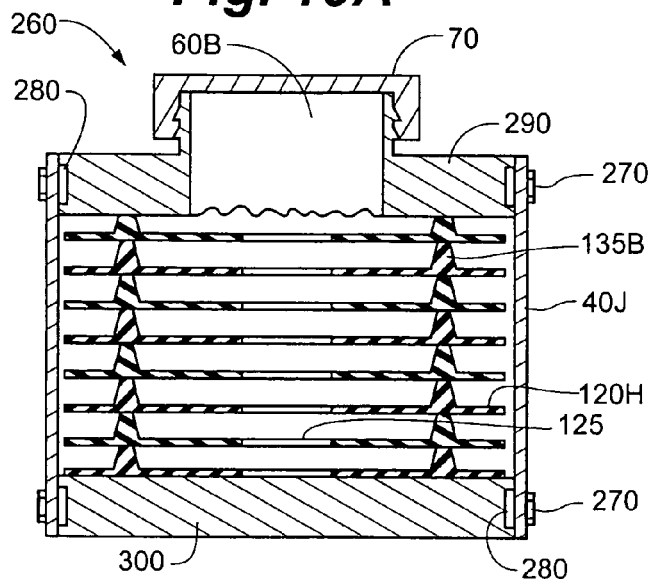
FIG. 19A is a cross-sectional view of a test fixture used to assess the ability to seed cells onto the upper and lower surfaces of a scaffold.
Figure 19B:
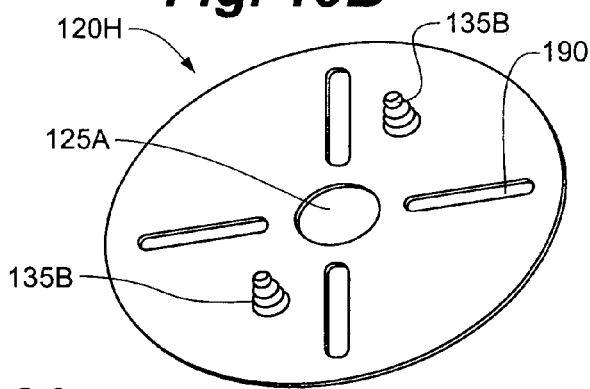
FIG. 19B shows one scaffold of the test fixture of FIG. 19A. Biological evaluations using this test fixture demonstrated the ability to culture cells in the absence of a gas/liquid interface when gas exchange occurred through the sidewall of the device, that a low gas permeable material surface area to attachment surface area is functional, that that a low gas permeable material surface area to medium volume is functional, and that cells can be cultured when the device is in the unrolled position or in the rolled position.

Gas Permeable Unrolled Cell Culture Device for Adherent Cell Culture Inoculated in the Vertical Position A test fixture was constructed to evaluate the capacity of a non-rolled, gas permeable cell culture device configured with more than one scaffold to culture cells relative to traditional flasks. FIG. 19A shows a cross-section of gas permeable test fixture 260. Scaffolds 120H were arranged vertically and a consistent gap was maintained between each scaffold 120H by spacers 135B. Wall 40J was gas permeable, comprised of silicone purchased from Medtronic Inc. (Minneapolis), approximately 0.0045 inches thick. Suture 270 applied force to gas permeable wall 40J, squeezing it against bulkhead gasket 280 to create a liquid tight seal between gas permeable wall 40J and upper bulkhead 290 and lower bulkhead 300. Medium access port 60B allowed fluid delivery to, and removal from, gas permeable test fixture 260. Cap 70 prevented contamination and was tightly closed during operation. FIG. 19B shows a perspective view of scaffold 120H. It was made of tissue culture treated polystyrene, 0.040 inches thick. Pipette access opening 125A, with a diameter of 0.75 inches, allowed pipette access and prevented gas from becoming trapped between scaffolds 120H. Four vent slots 190 allowed additional area for trapped gas to exit, ensuring that all gas/liquid interfaces were removed. The surface area per side of each scaffold 120H was about 86 cm$^2$. The inner diameter of gas permeable test fixture 260 was 4.4 inches and the internal height as measured from the inner surface of lower bulkhead 300 to the inner surface of upper bulkhead 290 was 2.25 inches. Thus, the gas permeable material surface area was 561 cm$^2$. Eight scaffolds 120H were stacked vertically with spacers 135B maintaining a gap of about 0.25 inch between each. The combined surface area of the tops of the eight scaffolds 120H was 695 cm$^2$. The internal volume of gas permeable test fixture 260 was approximately 500 ml. Therefore, the gas permeable material to medium volume ratio was 561 cm$^2$/500 ml, or 1.12 cm$^2$/ml.

$10.425 \times 10^6$ BHK cells, suspended in 500 ml Gibco GMEM medium supplemented with 1% Gibco Amino Acids Solution and 10% Hyclone FBS were inoculated into gas permeable test fixture 260P, creating a seeding density of 15,000 cells per cm$^2$ of attachment surface area. A control T-175 flask was also seeded with 15,000 cells per cm$^2$ of attachment surface area in 30 ml of the equivalent medium.

After approximately 96 hours, the cultures were terminated. Gas permeable test fixture 260 was disassembled and each of scaffolds 120H was microscopically examined, indicating a confluent pattern of cells was present on the upper surface of each of the eight scaffolds 120H. The control T-175 flask was also confluent as determined by microscopic evaluation. The T-175 flask and gas permeable test fixture 260 were trypsinized and standard cell counting techniques were used to determine the quantity of cells present. TABLE 6 summarizes the findings.

TABLE 6

Gas permeable cell culture device vs. T-flask

| Device | Total Cells($\times 10^6$) | Viability (%) | Medium Present(ml) | Height of Medium Above Cells ($cm^2$) |
|---|---|---|---|---|
| Gas permeable cell test fixture 260 | 220.8 | 98 | 500 | 0.72 |
| Control T-flask | 26.3 | 95 | 30 | 0.17 |

TABLE 6 demonstrates that cells were able to proliferate and remain healthy in the novel gas permeable test fixture 260, despite the absence of a gas/liquid interface.

The volume of space occupied by each device is noteworthy. Gas permeable test fixture 260 had a footprint of 100 $cm^2$ and a height, including the neck, of 7.6 cm. Thus, the space occupied was about 760 $cm^3$. The T-175 flask, including the neck, had a footprint approximately 23 cm long by 11 cm wide, and the body was about 3.7 cm tall. Thus, the space occupied was about 936 $cm^3$. Since gas permeable test fixture 260 cultured about 8.4 times more cells than the T-175 flask, it would take 8.4 T-175 flasks to yield an equivalent amount of cells over the same time period. TABLE 7 shows the difference in space that would be occupied if T-175 flasks were used to produce the same number of cells cultured by gas permeable test fixture 260, based on the experimental results of TABLE 6.

TABLE 7

| Device | Volume of space occupied per device($cm^3$) | Devices to produce 221 $\times 10^6$ cells in 3 days | Volume of space needed($cm^3$) |
|---|---|---|---|
| One novel gas permeable cell culture device 260 | 760 | 1 | 760 |
| Control T-flasks | 936 | 8.4 | 7862 |

The advantage of eliminating the gas/liquid interface is clear. Over a ten-fold reduction of space is obtained by gas permeable test fixture 260. This leads to cost savings in sterilization, shipping, storage, use of incubator space, and waste disposal. Furthermore, the number of devices that need to be handled is significantly reduced, leading to a dramatic labor and contamination risk reduction.

Example 7

Gas Permeable Unrolled Cell Culture Device for Adherent Cell Culture Inoculated in the Vertical and Inverted Position Using the test fixture shown in FIG. 19A, as previously defined in Example 6, an experiment was conducted to determine if cells would attach to both the top and bottom surfaces of the scaffolds. This could be accomplished by a two-step inoculation. In step one, a first inoculum was placed into the gas permeable test fixture while oriented in the vertical position. Cells were allowed to gravitate onto, and attach to the top surface of, the scaffolds over a 24-hour period. In step two, a second inoculum was placed into the gas permeable test fixture. Gas permeable test fixture was inverted to allow the cells of the second inoculum to gravitate onto, and attach to the bottom surface of, the scaffolds.

This process was undertaken, with each inoculation consisting of enough BHK cells to seed the exposed surfaces of the scaffolds at a density of 15,000 cells per $cm^2$. Medium composition was the same as that described in EXAMPLE 6. The time interval between the first inoculation and the second inoculation was twenty-four hours. The culture was terminated seventy-two hours after the second inoculation. The device was disassembled and each scaffold was microscopically assessed. Cells were uniformly distributed on both the top and bottom surfaces of each scaffold. Subsequently, the cells were removed using trypsin and a count was performed. The average quantity of live cells per $cm^2$ of surface area was $144 \times 10^5$, with viability greater than 99%.

Cells were thus able to attach and proliferate on the top and bottom of scaffold 120. Therefore, it is possible for the novel gas permeable cell culture device to be further reduced in size relative to conventional devices. For adherent cell culture, a wide variety of scaffold geometry can exist that have cell attachment area in any plane.

Example 8

Gas Permeable Unrolled Cell Culture Device for Adherent Cell Culture Inoculated in the Vertical and Inverted Position with Limited Distance between Scaffolds A test was conducted to determine if inserting more scaffold area into the device could further reduce device size. For additional space savings, the upper and lower surface of each scaffold was used to culture cells. The gas permeable test of Example 7 was fabricated with additional scaffolds. The number of scaffolds and distance between the scaffolds was chosen to create a volume to surface area ratio roughly equivalent to a traditional tissue culture flask. Recommended medium volume for a traditional T-175 flask varies from about 16-32 ml (Invitrogen Life Technologies). This dictates that medium reside about 0.09-0.18 cm from the attachment surface. The test device of this example was to be inoculated in two steps, allowing cells to reside on the upper and lower surfaces of each scaffold. Therefore, in order to get a conservative assessment of the value the gas permeable cell culture device can bring in terms of space and labor savings, 0.34 cm medium height was allowed to reside between each of the scaffolds. In this manner, the medium to surface area ratio was held constant relative to the T-175 flask. In effect, each scaffold surface had access to one half the medium between it, and the scaffold adjacent to it had access to the other half. Thus, the medium available to each side of a scaffold was consistent with the traditional tissue culture flask height of 0.17 cm per square centimeter of growth surface.

Fourteen scaffolds were inserted into the test device and evenly spaced approximately 0.34 cm apart. A T-175 flask, with 30 ml of medium residing at a height of 0.17 cm acted as a control. Inoculation using BHK cells was performed in two steps, as detailed in Example 7. Medium composition was the same as that described in Example 6. Seventy-two hours after the second inoculation, the culture was terminated and the device was disassembled and each scaffold was microscopically assessed for cell distribution upon the upper and lower surface. Each scaffold exhibited a distribution pattern on the upper and lower surface that was approximately equivalent to that of the T-175 flask. TABLE 7 shows an example of how increasing the surface area of the novel gas permeable cell culture device reduces the space needed to culture a given amount of cells when compared to the traditional T-175 flask. For example, when then novel gas permeable cell culture device contains 2432 cm² of scaffold surface area, fourteen T-175 flasks would be needed to provide equal surface area. If 1.7 mm of medium is intended to be available for each cm² of scaffold surface area, the volume of space occupied by the novel gas permeable cell culture device can be determined. TABLE 8 shows that in this case, the dramatically difference in the volume of space occupied by each type of device.

TABLE 8

Gas permeable device output with increased surface area

| Device | Available Surface area for cell attachment(cm²) | Number of devices needed | Volume of medium needed(cm³) | Volume of space occupied per device(cm³) |
|---|---|---|---|---|
| One novel gas permeable cell culture device | 2432 | 1 | 420 | 760 |
| T-175 flask | 2432 | 14 | 420 | 12,292 |

It can be seen that when the gas permeable cell culture device is designed to have the same medium to surface area ratio as the traditional flask, a much more efficient use of space results. The volume of space occupied by the gas permeable cell culture device is only one-sixteenth of that occupied by T-175 flasks when an equivalent amount of cells are desired. This translates directly into cost reductions for sterilization, shipping, storage, and disposal.

It is to be understood that the invention is not limited to the above embodiments, which are shown for purposes of illustration and described above, but is intended to include any modification or variation thereof falling within the scope of the appended claims.

Example 9

Gas Permeable Rolled Cell Culture Device for Adherent Cell Culture Inoculated in the Vertical Position Gas permeable test fixture 260 was constructed, as shown in the cross-sectional view of FIG. 19A and further defined in Example 5, to evaluate the capability of rolling a gas permeable cell culture device configured with more than one scaffold.

With gas permeable test fixture 260 in the vertical, unrolled position, 10.425×10⁶ BHK cells, suspended in 500 ml Gibco GMEM medium supplemented with 1% Gibco Amino Acids Solution and 10% Hyclone FBS were inoculated into gas permeable test fixture 260, creating a seeding density of 15,000 cells per cm² of attachment surface area. A control T-175 flask was also seeded with 15,000 cells per cm² of attachment surface area in 30 ml of the equivalent medium.

After approximately 24 hours, the gas permeable test fixture was places upon a standard roller rack at rotated at 1 RPM. Three days after the commencement of rolling, gas permeable test fixture was disassembled and each of the scaffolds was microscopically examined, indicating a confluent pattern of cells was present on the upper surface of each of the eight scaffolds. The control T-175 flask was also confluent as determined by microscopic evaluation.

This demonstrates that proliferation of cells is uninhibited by rolling the novel gas permeable cell culture device. Thus, creating a device that can be rolled or unrolled allows users greater options for protocol development.

| Guide to Reference Characters in Drawings | |
|---|---|
| 10 | gas permeable cell culture device |
| 12 | gas permeable wall test fixture |
| 14 | multiple scaffold test fixture |
| 15 | gas permeable multiple well plate |
| 16 | gas permeable wall multiple well plate |
| 20 | cells |
| 25 | buoyant shoulder |
| 30 | lower gas permeable material |
| 31 | non-gas permeable bottom |
| 40 | walls |
| 41 | gas permeable wall |
| 42 | interior walls |
| 45 | individual wells |
| 46 | high surface area well |
| 50 | medium |
| 55 | top cover |
| 60 | medium access port |
| 65 | septum |
| 70 | cap |
| 75 | o-ring |
| 80 | lower gas permeable material support |
| 90 | gas compartment |
| 95 | feet |
| 100 | lower gas access openings |
| 105 | tubular test fixtures |
| 110 | projections |
| 115 | mesh |
| 120 | scaffolds |
| 125 | pipette access opening |
| 130 | inoculum |
| 135 | spacer |
| 145 | spring arm |
| 150 | ramps |
| 160 | elevation posts |
| 170 | scaffold locator screw |
| 180 | rotation arrow |
| 190 | vent slots |
| 200 | gas permeable wall |
| 201 | top wall |
| 210 | non-gas permeable wall |
| 212 | tongue |
| 215 | groove |
| 220 | fluid delivery port |
| 230 | fluid removal port |
| 240 | attachment scaffold |
| 241 | enclosure |
| 260 | gas permeable test fixture |
| 270 | suture |
| 280 | bulkhead gasket |
| 290 | upper bulkhead |
| 300 | lower bulkhead |

Those skilled in the art will recognize that numerous modifications can be made to this disclosure without departing from the spirit on the inventions described herein. Therefore, it is not intended to limit the breadth of the invention to the embodiments illustrated and described. Rather, the scope of the invention is to be interpreted by the appended claims and their equivalents. Each publication, patent, patent application, and reference cited herein is hereby incorporated herein by reference.

What is claimed is:

1. A cell culture device for the culture of animal cells comprising:
a container with a top, a bottom, at least one sidewall, at least one access port, wherein at least one said sidewall is comprised at least in part of gas permeable material; and
more than one scaffold for cells to reside upon with a space separating at least two of said scaffolds, at least one of said scaffolds not being oriented parallel to at least one said gas permeable sidewall, said cell culture device including structure to allow medium to reside above each scaffold in the absence of gas/liquid interface residing above each of said scaffolds during use, and not in communication with equipment to mix or perfuse a cell culture medium.

2. The device of claim 1 wherein said container is in the form of a multiple well tissue culture plate.

3. The device of claim 1 said scaffolds arranged one above the other.

4. The device of claim 1 wherein each of said scaffolds generally reside an equal distance apart.

5. The device of claim 3 wherein at least one of said scaffolds includes at least one spring arm.

6. The device of claim 1 wherein said sidewall is comprised of flexible material.

7. The device of claim 6 wherein at least one of said scaffolds includes at least one spring arm.

8. The device of claim 1 wherein at least one said scaffold is comprised of plastic.

9. The device of claim 8 wherein at least one said scaffold is connected to said sidewall.

10. The device of claim 1, at least one scaffold being offset from the remaining scaffolds in order to allow the offset scaffold to be assessed microscopically.

11. The device of claim 1 wherein said container is in the shape of a roller bottle so that the device can be rolled in a roller rack.

12. The device of claim 1 wherein said gas permeable material includes dimethyl silicone.

13. The device of claim 12 wherein said dimethyl silicone is 0.015 inch thick or less.

14. The device of claim 1 wherein the ratio of the surface area of said gas permeable material to the surface area of said scaffold is at least 0.039 $cm^2/cm^2$.

15. The device of claim 1 wherein at least one of said scaffolds includes at least one spring arm.

16. The device of claim 7 wherein said scaffolds includes spring arms.

17. The device of claim 1 wherein at least one of said scaffolds include at least one ramp and at least one of said scaffolds includes at least one spring arm.

18. A mammalian cell culture device comprising:
a container with a top, a bottom, at least one sidewall, at least one access port, at least one said sidewall being comprised at least in part of gas permeable material;
more than one scaffold for cells to reside upon with a space separating at least two of said scaffolds, at least one of said scaffolds not being oriented parallel to at least one said gas permeable sidewall, said cell culture device including structure to allow medium to reside above each scaffold in the absence of gas/liquid interface residing above each of said scaffolds during use, and not in communication with equipment to mix or perfuse a cell culture medium.

* * * * *

UNITED STATES PATENT AND TRADEMARK OFFICE
CERTIFICATE OF CORRECTION

PATENT NO. : 8,415,144 B2
APPLICATION NO. : 11/505122
DATED : April 9, 2013
INVENTOR(S) : Wilson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 899 days.

Signed and Sealed this
Third Day of March, 2015

Michelle K. Lee
*Deputy Director of the United States Patent and Trademark Office*